(12) United States Patent
Coen et al.

(10) Patent No.: US 7,893,108 B2
(45) Date of Patent: Feb. 22, 2011

(54) ANTIVIRAL METHODS AND COMPOSITIONS

(75) Inventors: Donald M. Coen, Boston, MA (US); Arianna Loregian, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 890 days.

(21) Appl. No.: 11/652,369

(22) Filed: Jan. 11, 2007

(65) Prior Publication Data

US 2007/0225310 A1 Sep. 27, 2007

Related U.S. Application Data

(63) Continuation-in-part of application No. PCT/US2005/025058, filed on Jul. 14, 2005.

(60) Provisional application No. 60/587,972, filed on Jul. 14, 2004.

(51) Int. Cl.
*A61K 31/175* (2006.01)
(52) U.S. Cl. .................. 514/583; 514/581; 514/582
(58) Field of Classification Search .......... 514/150, 514/581–583
See application file for complete search history.

(56) References Cited

U.S. PATENT DOCUMENTS

| | | | |
|---|---|---|---|
| 3,869,496 | A | 3/1975 | Andrews et al. |
| 5,290,686 | A | 3/1994 | Kendal et al. |
| 5,663,161 | A | 9/1997 | Bell |
| 6,342,492 | B1 | 1/2002 | Bell |
| 6,872,395 | B2 | 3/2005 | Kawaoka |
| 2002/0019423 | A1 | 2/2002 | Bell |
| 2003/0194694 | A1 | 10/2003 | Kawaoka |
| 2005/0032245 | A1 | 2/2005 | Coen et al. |
| 2005/0232950 | A1 | 10/2005 | Kawaoka |
| 2006/0247161 | A1 | 11/2006 | Planz et al. |
| 2007/0172489 | A1 | 7/2007 | Ludwig et al. |
| 2007/0270443 | A1 | 11/2007 | Went et al. |
| 2008/0076669 | A1 | 3/2008 | Mehtali |

FOREIGN PATENT DOCUMENTS

| | | |
|---|---|---|
| EP | 0454058 | 10/1991 |
| GB | 1047297 | 11/1966 |
| WO | WO-92/07856 | 5/1992 |
| WO | WO-92/18616 | 10/1992 |
| WO | WO-93/03173 | 2/1993 |
| WO | WO-96/25167 | 8/1996 |
| WO | WO-98/39287 | 9/1998 |
| WO | WO-00/34268 | 6/2000 |
| WO | WO-00/68185 | 11/2000 |
| WO | WO-01/79273 | 10/2001 |
| WO | WO-02/095054 | 11/2002 |
| WO | WO-03/053972 | 7/2003 |

(Continued)

OTHER PUBLICATIONS

Testa "Prodrug research: futile or fertile," Biochemical Pharmacology, 2004, vol. 68, pp. 2097-2106.*

(Continued)

*Primary Examiner*—Shengjun Wang
(74) *Attorney, Agent, or Firm*—Foley Hoag, LLP

(57) ABSTRACT

Disclosed herein are antiviral compounds, such as anti-human cytomegalovirus antiviral compounds, pharmaceutical compositions and antiviral methods.

3 Claims, 15 Drawing Sheets

FOREIGN PATENT DOCUMENTS

| | | |
|---|---|---|
| WO | WO-2004/060360 | 7/2004 |
| WO | WO-2004/085682 | 10/2004 |
| WO | WO-2006/019955 | 2/2006 |
| WO | WO-2006/046134 | 5/2006 |
| WO | WO-2007/092457 | 8/2007 |
| WO | WO-2007/136737 | 11/2007 |

OTHER PUBLICATIONS

Vancikova et al. "Cytomegalovirus Infection in immunocompetent and immunocompromised individuals—A Review," Current Drug Targets, Immune, Endocrine & Metabolic Disorders, 2001, vol. 1, No. 2, pp. 179-187.*

Appleton et al.; "Crystal Structure of the Cytomegalovirus DNA Polymerase Subunit UL44 in Complex with the C Terminus from teh Catalytic Subunit"; *The Journal of Biological Chemistry*, vol. 281, Feb. 24, 2006, pp. 5224-5232.

Bence et al.; "Aminoanthraquinones as Novel Ligands at the Polyamine Binding Site on the *N*-Methyl-D-aspartate Receptor Complex"; *Bioorganic & Medicinal Chemistry Letters* 10 (2000) pp. 2621-2623.

Loregian et al.; "Selective anit-cytomegalovirus compounds discovered by screening for inhibitors of subunit interactions of the viral polymerase"; *Chem. Biol.* Feb. 13, 2006 (2); pp. 191-200.

Loregian et al.; "Residues of Human Cytomegalorivus DNA Polymerase Catalytic Subunit UL54 That Are Necessary and Sufficient for Interaction with the Accessory Protein UL44"; *Journal of Virology*; vol. 78, No. 1, Jan. 2004; pp. 158-167.

Loregian et al.; "Specific Residues in the Connector Loop of the Human Cytomegalovirus DNA Polymerase Accessory Protein UL44 Are Crucial for Interaction with the UL54 Catalytic Subunit"; *Journal of Virology*, Sep. 2004, vol. 78, No. 17; pp. 9084-9092.

Database CA, Mikhailova et al., "Protonation of Anthrapyridone and Its Amino Derivatives. Monoprotonated form of Anthrapyridoneas a Heteroanalog of Benzophonalenone," Zhurnal Organicheskoi Khimii, 15(7):1516-25, (1979), Database Accession No. 1979:592612, XP002361940.

Database Registry, "3H-Naphtho[1,2,3-de]quinoline-2, 7-dione, 3-methyl-6-(4-morpholinyl)-(9Cl) (CA Index Name)," Zelinsky Institute of Organic Chemistry, (Dec. 18, 2000), Database Accession No. 309277-07-4, XP002361940.

Database Registry, "3H-Naphtho[1,2,3-de]quinoline-2, 7-dione, 3-methyl-6-(1-pyrrolidinyl)-(9Cl)," ChemBridge Corporation (Jun. 4, 2002), Database Accession No. 425402-29-5, XP002361941.

Database Registry, "3H-Naphtho[1,2,3-de]quinoline-2, 7-dione, 3-methyl-6-(4-methyl-1-piperidinyl)-(9Cl)," Otava (Apr. 2, 2004), Database Accession No. 670259-09-3, XP002361942.

Database Registry, (May 18, 2004), Database Accession No. 682786-79-4, XP002361943.

* cited by examiner

Figure 2

Table 1

| Compound | RP assay IC50 (µM) | UL54 activity IC50 (µM) | Ie DNA synth. assay IC50 (µM) | ELISA Interac. assay IC50 (µM) | Cytotoxicity CC50 (µM) 24 hrs | Cytotoxicity CC50 (µM) 72 hrs | Cytotoxicity CC50 (µM) 120 hrs | Plaque reduct. assay IC50 (µM) | Viral yield assay IC50 (µM) 72 hrs | Viral yield assay IC50 (µM) 120 hrs |
|---|---|---|---|---|---|---|---|---|---|---|
| AL1 | >200/>100 (±) | >100 | >100 | | >200 | >100/>200 | >200 | >30/160 (±) | | 50 |
| AL2 | >200/>100 (±) | >100 | >100 | | >200 | >100/>200 | >200 | >30 (±) | | 90 |
| AL3 | >200/>100 (±) | 95 | >100 | >100 | >200 | >100/>200 | >200 | >30/85 (±) | | 80 |
| AL4 | >200/>100 (-) | >100 | | | >200 | >100/200 | >200 | >30 (±) | | >100 |
| AL5 | 15/7 | >100 | 5 | 8 | 70 | 90/80 | 80 | 2.1 | 1.1 | 1 |
| AL6 | 10/30 | >100 | | | 50 | 20/7 | 20 | >90 (-) | | |
| AL7 | >200/>200 (-) | >100 | | | >200 | 50/60 | 120 | 35 | | |
| AL8 | 0.8/7 | >100 | | | >200 | >100/60 | 60 | >30 (-) | | |
| AL9 | 20/11 | >100 | 10 | 20 | >200 | 50/60 | 70 | 12 | 9 | 3 |
| AL10 | 20/7 | >100 | | | 20 | 1/0.7 | 3 | 0.2 | | |
| AL11 | 6/2 | >100 | | | 200 | 7/12 | 10 | >30 (-) | | |
| AL12 | 10/20 | >100 | 15 | 12 | >200 | 40/40 | 35 | 1.8 | 2 | 3.5 |
| AL13 | 200/40 | >100 | | | >200 | 15/20 | 18 | 12.5 | | |
| AL14 | >200/>200 (-) | >100 | | | >200 | 20/40 | 30 | 9 | | |
| AL15 | 120/60 | >100 | | | >200 | 65/40 | 55 | >30 (-) | | |
| AL16 | >200/>200 (-) | >100 | | | 18 | 2/2 | 4 | 6 | | |
| AL17 | >200/>200 (-) | >100 | | | >200 | >100/150 | >200 | >30 (-) | | |
| AL18 | 40/30 | >100 | | | >200 | 100/80 | 200 | 1.2 | 0.3 | 0.4 |
| AL19 | >200/>200 (-) | >100 | 5 | 9 | 18 | 1/1 | 2 | 4 | | |
| AL20 | >200/>200 (-) | >100 | >100 | >100 | >200 | >100/120 | 200 | 1.2 | | 12 |
| AL21 | 20/10 | 78 | 5 | 10 | >200 | 30/50 | 80 | 3.5 | 1.8 | 3 |
| BP5 | >200/>200 (-) | 40 | 20 | 15 | 30 | 12/12 | 13 | 2 | | |
| UL54 pept. | 6 | >100 | 18 | | | | | | | |

Table 2

| Compound | Fluorescence Polarization IC$_{50}$ (μM) | ELISA Interaction IC$_{50}$ (μM) | Long-Chain DNA Synthesis by UL54/UL44 IC$_{50}$ (μM) | DNA Synthesis by UL54 Alone IC$_{50}$ (μM) | Plaque Reduction ED$_{50}$ (μM) | Viral Yield ED$_{50}$ (μM) 72 hrs | Viral Yield ED$_{50}$ (μM) 120 hrs | Cytotoxicity CC$_{50}$ (μM) 24 hrs | Cytotoxicity CC$_{50}$ (μM) 72 hrs | Cytotoxicity CC$_{50}$ (μM) 120 hrs |
|---|---|---|---|---|---|---|---|---|---|---|
| AL1 | >200 | | >100 | >100 | >30 | | 50 | >200 | >200 | >200 |
| AL2 | >200 | | >100 | 95 | >30 | | 90 | >200 | >200 | >200 |
| AL3 | >200 | >200 | >100 | >100 | >30 | >100 | 80 | >200 | >200 | >200 |
| AL4 | >200 | | | >100 | >30 | | >100 | >200 | >200 | >200 |
| AL5[a] | 5 | 7 | 5 | >100 | 2.2 | 1.3 | 1.0 | 110 | 95 | 75 |
| AL6 | 30 | | | >100 | >30 | | | 50 | 20 | 20 |
| AL7 | >200 | | | >100 | >30 | | | >200 | 60 | 120 |
| AL8 | 6 | | | >100 | >30 | | | >200 | 60 | 60 |
| AL9 | 21 | 19 | 10 | >100 | 10 | 8.0 | 3.1 | >200 | 60 | 70 |
| AL10 | 6 | | | >100 | 0.1 | | | 20 | 1 | 3 |
| AL11 | 6 | | | >100 | >30 | | | 200 | 12 | 10 |
| AL12 | 19 | 12 | 15 | >100 | 1.4 | 1.9 | 3.2 | >200 | 40 | 35 |
| AL13 | 50 | | | >100 | 10 | | | >200 | 17 | 18 |
| AL14 | >200 | | | >100 | 7.0 | | | >200 | 30 | 30 |
| AL15 | 60 | | | >100 | 5.5 | | | >200 | 57 | 55 |
| AL16 | >200 | | | >100 | >30 | | | 18 | 2 | 4 |
| AL17 | >200 | | | >100 | >30 | | | >200 | >200 | >200 |
| AL18 | 30 | 9 | 5 | >100 | 1.1 | 0.3 | 0.4 | >200 | 100 | 200 |
| AL19 | >200 | >200 | >100 | >100 | 4.0 | | | 18 | 1 | 2 |
| AL20 | >200 | 10 | 5 | >100 | 1.3 | 1.7 | 4.0 | >200 | 120 | 200 |
| AL21 | 10 | 15 | 18 | 78 | 3.0 | | 3.5 | >200 | 45 | 80 |
| peptide 1 | 5 | | | >100 | 1.9 | 0.9 | 0.8 | >200 | 200 | 200 |
| GCV | | | | | | | | >200 | 200 | 180 |

[a] Data for the five compounds that were active in both biochemical and antiviral assays are highlighted in bold.

Figure 3

Figure 4
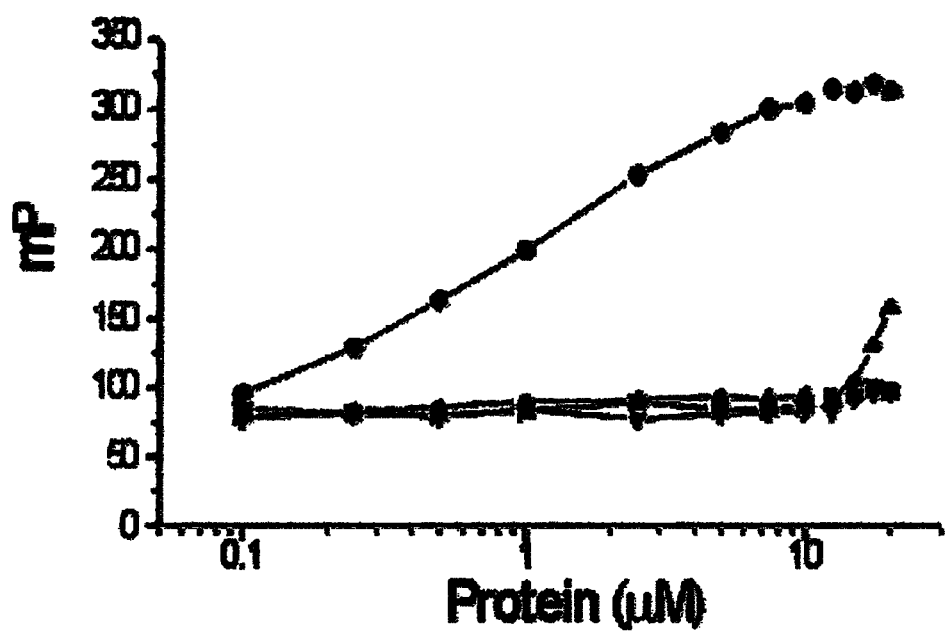
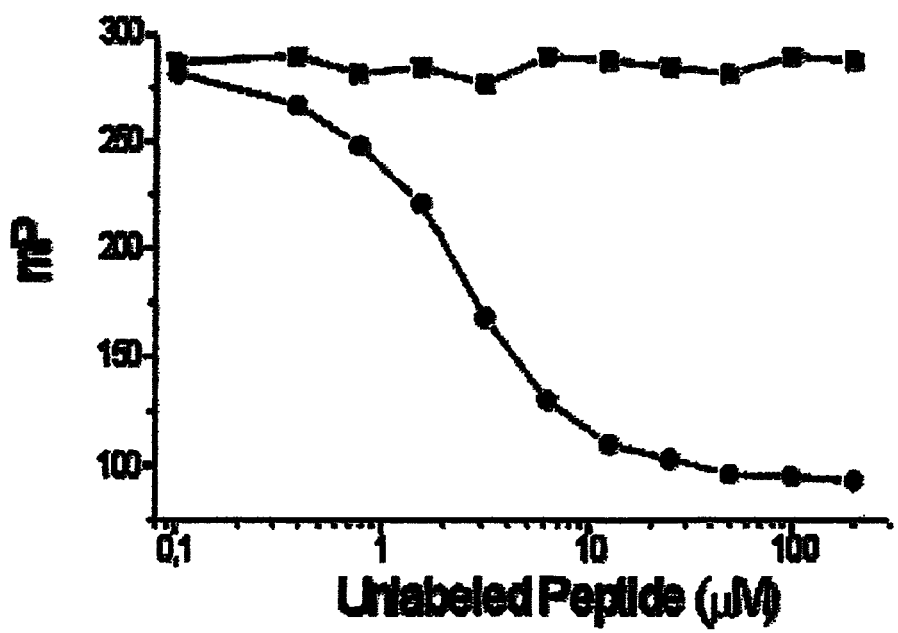

Figure 5
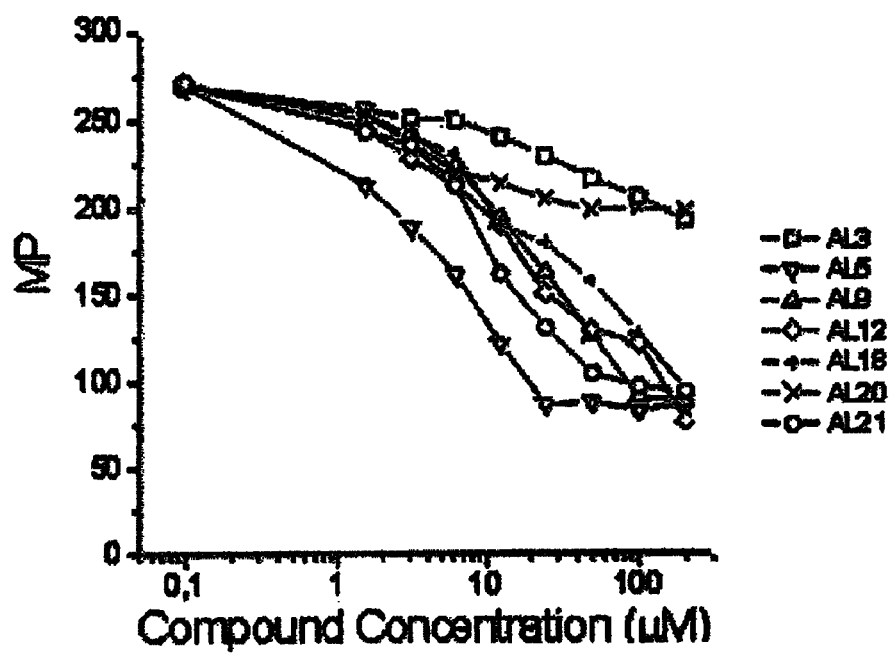
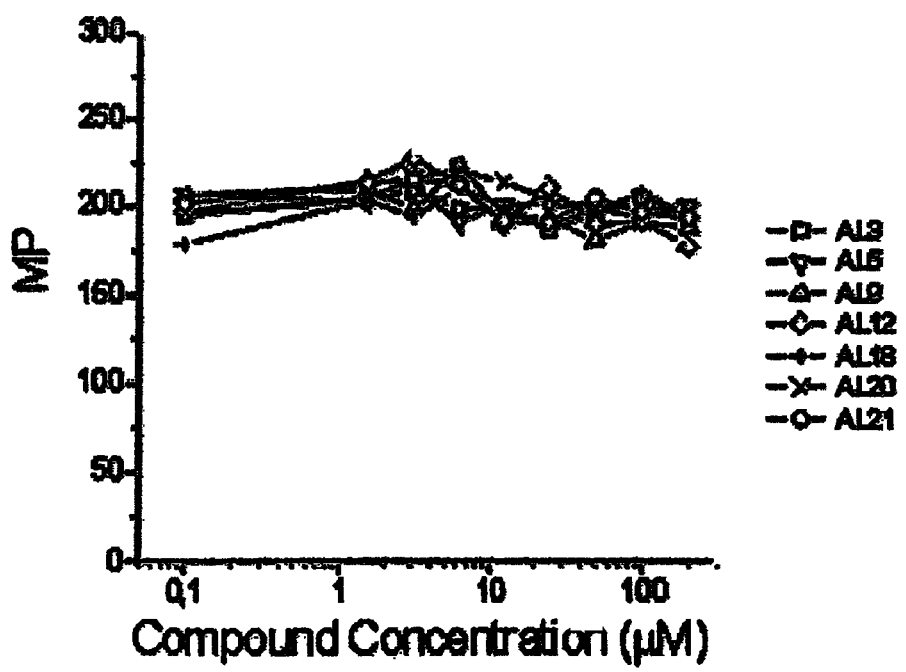

Figure 7
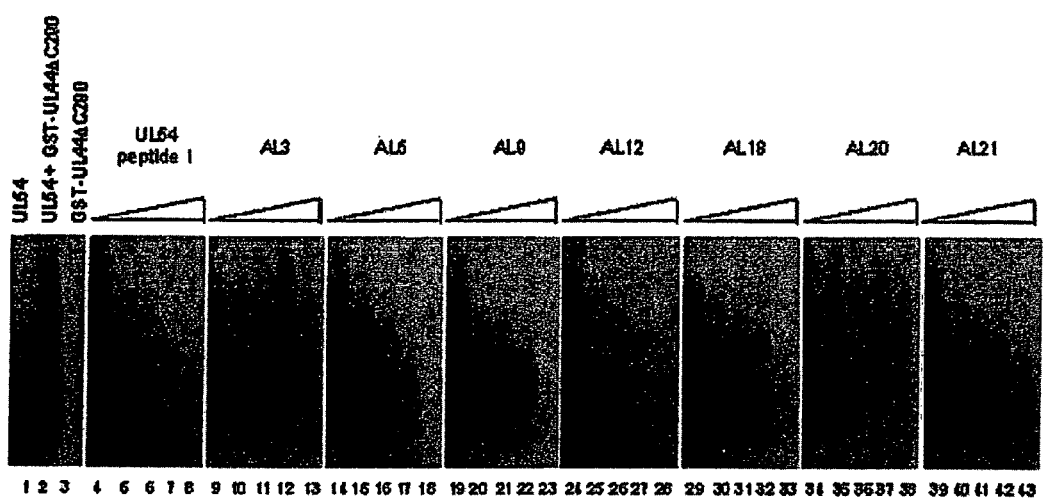
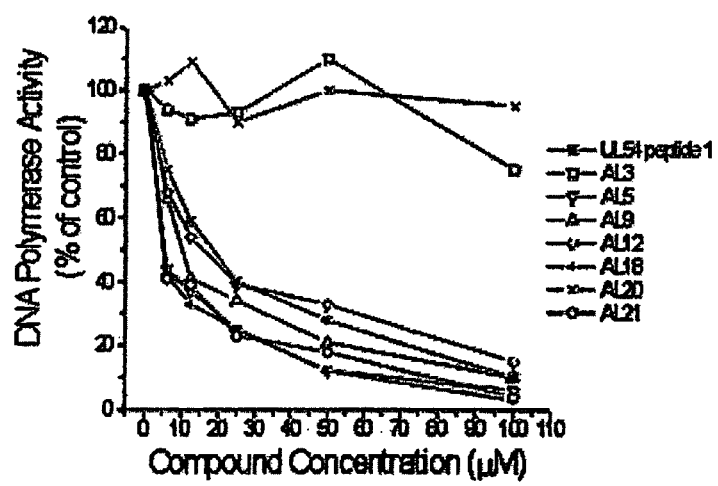

Figure 9
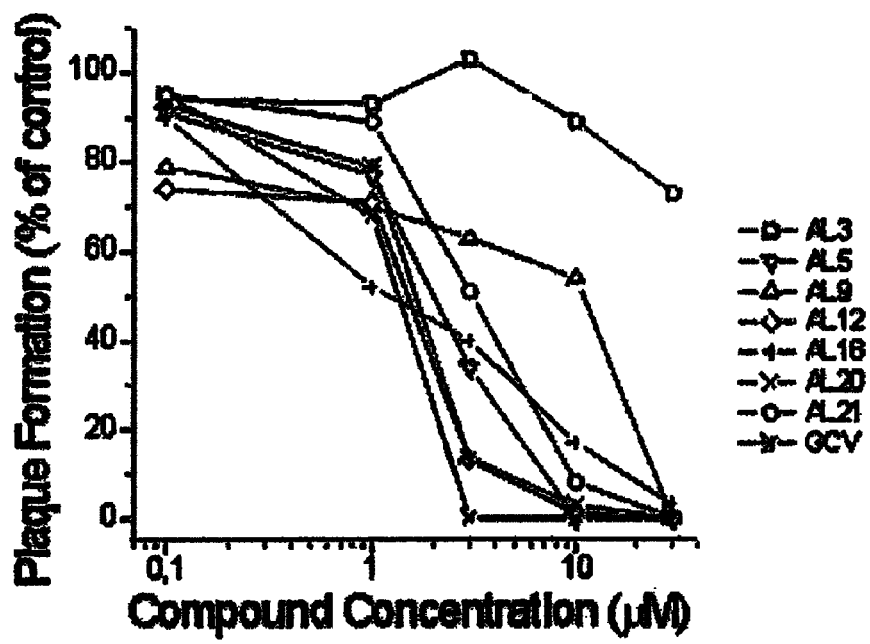
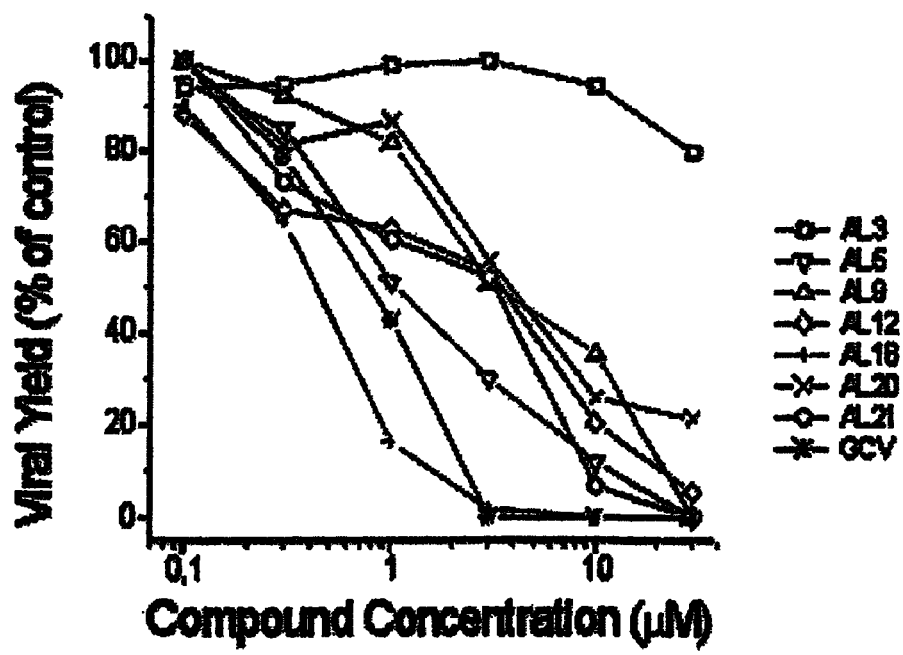

Figure 14

| Compound | HCMV AD169 (wild-type) ED$_{50}$ (µM) | HCMV 759rD100-1 (GCV-resistant) ED$_{50}$ (µM) | HCMV PFArD100 (PFA-resistant) ED$_{50}$ (µM) |
|---|---|---|---|
| AL3 | >30 | >30 | >30 |
| AL5 | 2.2 | 4.5 | 1.8 |
| AL9 | 10 | 7 | 3.0 |
| AL12 | 1.4 | 3 | 0.6 |
| AL18 | 1.1 | 0.5 | 2.3 |
| AL20 | 1.3 | 4.5 | 20 |
| AL21 | 3.0 | 4.1 | 3.0 |
| GCV | 1.9 | 12 | 1.5 |
| PFA | 38 | 39 | 300 |

ANTIVIRAL METHODS AND COMPOSITIONS

RELATED APPLICATIONS

This application claims the benefit of PCT/US05/025058, filed Jul. 14, 2005, which claims priority to U.S. Provisional Application No. 60/587,972, filed Jul. 14, 2004, the contents of which are both incorporated by reference herein in their entirety.

GOVERNMENTAL SUPPORT

This invention was made with government support under RO1 AI19838 and RO1 AI26077 awarded by the National Institutes of Health. The government has certain rights in the invention.

BACKGROUND OF THE INVENTION

Protein-protein interactions play a pivotal role in virtually every biological process, including the replication of pathogenic viruses in host cells. Due in part to their importance for virus replication, several interactions between viral proteins have been proposed as attractive targets for antiviral drug discovery, as the exquisite specificity of such interactions affords the possibility of interfering with them in a highly selective and effective manner (Loregian et al., 2002). We have been investigating one such interaction—that between the two subunits of the DNA polymerase of human cytomegalovirus ("HCMV")—as a new drug target (Loregian et al., 2004a; Loregian et al., 2004b; Loregian et al., 2003). HCMV is a member of the DNA herpes virus family. HCMV has been isolated from saliva, urine, breast milk, blood, semen, and vaginal secretions. It can be transmitted in utero, despite the presence of high maternal antibody titers. Once infected, the individual conserves the virus in a latent or persistent form throughout life.

HCMV is an ubiquitous herpesvirus. Although it rarely causes symptomatic disease in immunocompetent individuals, it is responsible for a variety of severe diseases, including pneumonia, gastrointestinal disease and retinitis, in transplant recipients and in AIDS patients (Pass, 2001). HCMV is also a major cause of congenital malformation in newborn children, often resulting in deafness and mental retardation (Trincado et al., 2000). Antiviral agents currently licensed for the treatment of HCMV infections include ganciclovir (GCV), foscarnet, and cidofovir, all of which inhibit the viral DNA polymerase). Ganciclovir and cidofovir are nucleoside analogs which function as DNA chain terminators, whereas foscarnet inhibits HCMV DNA polymerase through binding to its pyrophosphate binding site. However, these drugs are limited by their toxicities, pharmacokinetic drawbacks, and/or viral resistance issues. Thus, there is considerable need for new anti-HCMV compounds.

Serological surveys indicate that most adults have been infected with HCMV. Following primary infection, which is almost always asymptomatic in people with normal immunity, the virus establishes latency. The virus is probably maintained at least in part in this latent state by immune surveillance mechanisms since immunosuppression frequently leads to reactivation of the virus. Reactivation of HCMV in immunosuppressed individuals can give rise to life-threatening disease.

HCMV infections are manifested in a variety of disease states. Infection with HCMV during pregnancy can lead to congenital malformation resulting in mental retardation and deafness. Infections of premature newborns can also result in significant morbidity. Although most infections of older immunocompetent individuals do not result in obvious disease, in young children they can sometimes be expressed as severe respiratory disease, and in older children and adults, they are sometimes expressed as anicteric hepatitis and mononucleosis.

HCMV pneumonitis is the most common single cause of death following bone marrow transplantation, and disseminated HCMV infection is a major cause of mortality and morbidity in patients with solid organ transplants or with AIDS. There is also evidence of a link between HCMV and atherosclerosis.

Like other herpes viruses, HCMV has a propensity to reactivate, particularly in immunosuppressed patients. Thus, HCMV infections present a major clinical problem for AIDS patients and other immunocompromised individuals such as organ transplant recipients and other patients receiving immunosuppressive drugs. Among AIDS patients, HCMV is the causative agent of certain invasive diseases such as retinitis, which is sight threatening, peripheral retinitis (an earlier form of the infection), esophagitis, and colitis.

In modern medical practice, HCMV is a significant pathogen whose ultimate control by means of immunization or drug therapy has become an important objective. So far, preliminary vaccination efforts have been unsuccessful, and no ideal therapeutic agent has been developed which can efficiently contain HCMV infection. Prophylaxis and therapy using HCMV immune globulins have met with only moderate success. In addition, therapeutic agents developed for treating HCMV infections have the common disadvantages of some type of toxicity to the host and the inability to rid the host of latent infection.

A major obstacle in developing suitable drugs possessing antiviral activity against HCMV is the ability to distinguish between the virus and the patient's own cells. HCMV, like other viruses, can only replicate by physically invading a cell and using the cell's biochemical pathways to make new viral proteins.

Because virus replication cycles are intimately connected with the functions of the host cell, there are few features peculiar to the virus that are not also present in the host. This makes selective attack on the virus difficult. Therefore, antiviral compounds generally represent a compromise between suppression of virus replication while minimizing adverse effects on the host.

Another obstacle to the inhibition of protein-protein interactions is that these interactions often involve a large surface area and multiple contacts (Archakov et al., 2003; Tsai et al., 1997). However, several studies have shown that relatively few residues within these large surfaces can drive binding (Cunningham and Wells, 1997) and that single substitutions in one subunit of a protein-protein interface can completely disrupt subunit interactions or nearly so (Eubanks et al., 2000; Imai et al., 2000; Koltzscher and Gerke, 2000; Lomax et al., 1998; Ramadevi et al., 1998; Sengchanthalangsy et al., 1999; Stenberg et al., 2000; Thomas et al., 1998). We have previously investigated this issue with the HCMV DNA polymerase, which consists of a 1242-residue catalytic subunit, UL54 (Cihlar et al., 1997; Kouzarides et al., 1987; Nishiyama et al., 1983), and a 433-residue accessory protein, UL44, which has been proposed to act as a processivity factor (Ertl and Powell, 1992; Weiland et al., 1994). We found that single substitutions in either UL54 or UL44 can drastically and specifically disrupt the interaction of these two proteins and their ability to synthesize long chains of DNA (Loregian et al., 2004a; Loregian et al., 2004b). Both UL54 and UL44 are essential for HCMV DNA replication (Pari and Anders, 1993; Pari et al., 1993; Ripalti et al., 1995) and the UL54-UL44 interaction is specific (Loregian et al., 2003). Additionally, a peptide corresponding to the C-terminal 22 residues of UL54 can both disrupt the physical interaction between UL54 and UL44 and specifically inhibit the stimulation of UL54 activity by the accessory protein (Loregian et al., 2003). Taken together these observations suggest that a small molecule could specifically inhibit the UL54-UL44 interaction and HCMV replication.

Although there are only a few examples of small molecules that disrupt protein-protein interactions and exert effects inside cells (reviewed in (Arkin and Wells, 2004; Cochran, 2000; Toogood, 2002)), we were encouraged by the recent identification of a small molecule (BP5) that specifically inhibits the physical interaction between the two subunits of herpes simplex virus type 1 (HSV-1) DNA polymerase, UL30 and UL42, which are homologous to UL54 and UL44, respectively, as well as HSV-1 replication in infected cell cultures (Pilger et al., 2004). Thus, the goal of this study was to determine if we could identify, via high throughput screening, compounds that could specifically inhibit the UL54-UL44 interaction. These studies led to the discovery of several small molecules with selective anti-HCMV activity.

SUMMARY OF THE INVENTION

Disclosed herein are compounds having a formula selected from the group consisting of formulas 1-17, such as the compounds set forth in FIGS. 1a and 1b, or pharmaceutically acceptable salts, prodrugs or esters thereof. These compounds may be in the form of a pharmaceutical composition including a pharmaceutically acceptable vehicle. Compounds may also be included in a device, such as a syringe, for administration to a subject.

Further provided are methods for preparing pharmaceutical compositions, comprising combining a compound having a formula selected from the group consisting of formulas 1-17 or a pharmaceutically acceptable salt, prodrug or ester thereof with a pharmaceutically acceptable vehicle.

Also described herein are methods for treating or preventing a viral infection in a subject, such as an infection by human cytomegalovirus (HCMV), comprising administering to a subject in need thereof a pharmaceutically effective amount of a compound described herein, to thereby treat or prevent an infection by HCMV.

These embodiments of the present invention, other embodiments, and their features and characteristics, will be apparent from the description, drawings and claims that follow.

BRIEF DESCRIPTION OF THE DRAWINGS

FIG. 2 sets forth Table 1.

FIG. 3 sets forth Table 2.

FIG. 4 depicts the results of the FP assay: (A) Increasing concentrations of wild-type GST-UL44ΔC290 (●), of GST-UL44ΔC290 I135A, a mutant UL44 which does not bind UL54 (▲), of GST (■), or of MBP-UL42ΔC340 (▼) were added to 3 nM of a fluorescently labeled peptide corresponding to the C-terminal 22 residues of HCMV UL54 (peptide 1), and FP (as millipolarization units, mP) was measured. (B) Increasing concentrations of unlabeled peptide 1 (●), or of peptide A, corresponding to the 36 C-terminal residues of HSV-1 UL30 (■), were added to reaction mixtures containing 2.5 μM GST-UL44ΔC290 and 3 nM labeled peptide 1, and FP was measured.

FIG. 5 depicts dose-dependence of inhibition of FP of selected compounds: (A) Increasing concentrations of compound AL3, AL5, AL9, AL12, AL18, AL20, and AL21, were added to reaction mixtures containing 2.5 μM GST-UL44ΔC290 and 3 nM labeled peptide 1, and FP (as millipolarization units, mP) was measured; (B) Increasing concentrations of compound AL3, AL5, AL9, AL12, AL18, AL20, and AL21, were added to reaction mixtures containing 7 μM MBP-UL42ΔC340 and 5 nM of a fluorescently labeled peptide corresponding to the C-terminal 18 residues of HSV-1 UL30, and FP was measured.

FIG. 7 depicts the effect of selected compounds on long-chain DNA synthesis by UL54 and UL44. (A) Long-chain DNA synthesis directed by in vitro expressed UL54 in the presence of purified GST-UL44ΔC290 protein was assayed by measuring the incorporation of labeled [$^{32}$P]TTP using a poly(dA)-oligo(dT) template following addition of increasing concentrations (6.25, 12.5, 25, 50, 100 μM) of peptide 1 (lanes 4 to 8) or of compound AL3 (lanes 9 to 13), AL5 (lanes 14 to 18), AL9 (lanes 19 to 23), AL12 (lanes 24 to 28), AL18 (lanes 29 to 33), AL20 (lanes 34 to 38), and AL21 (lanes 39 to 43). As controls, long-chain DNA synthesis directed by UL54 alone (lane 1), GST-UL44ΔC290 alone (lane 3), and by UL54 in the presence of GST-UL44ΔC290 with no compound added (lane 2) were also assayed. The reaction products were visualized by autoradiography following electrophoresis on a 4% alkaline agarose gel. (B) Autoradiographs such those in (A) were quantified by phosphorimager and the percentage of signal at each concentration of compound relative to that in the absence of added compounds was plotted versus the concentration of each compound tested.

FIG. 9 depicts antiviral activity of selected compounds. (A) The effects of AL3, AL5, AL9, AL12, AL18, AL20, AL21, and GCV as a control, on plaque formation by HCMV strain AD169 were determined in HFF cells. (B) The effects of AL3, AL5, AL9, AL12, AL18, AL20, AL21, and GCV as a control, on the yield of HCMV AD169 in HFF cells were determined at 5 days post-infection in single-cycle growth assays.

FIG. 14 depicts a table of activities of AL compounds against different HCMV strains (as tested by plaque reduction assays).

DETAILED DESCRIPTION OF THE INVENTION

Definitions

Figure 1A:
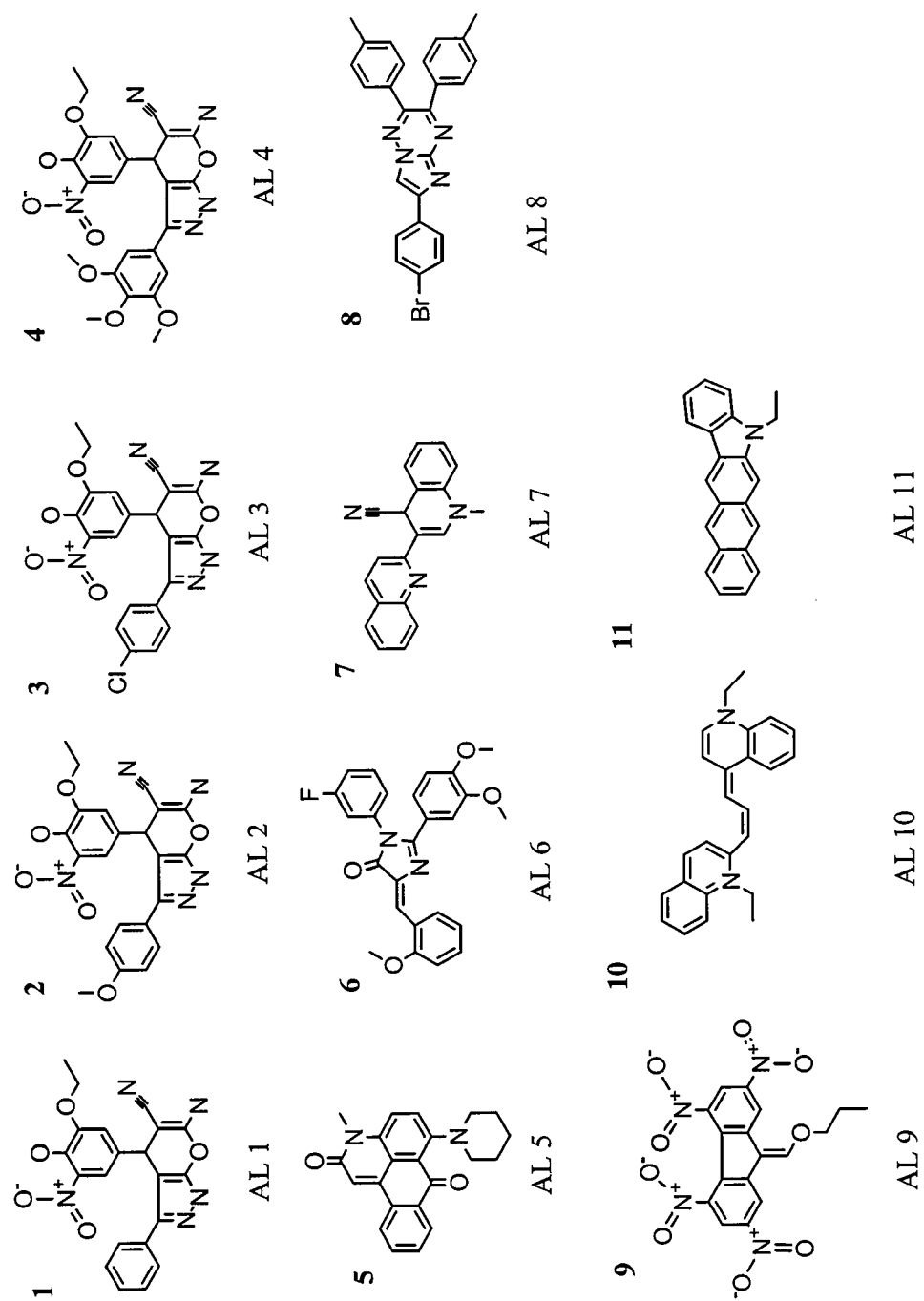
FIGS. 1a and 1b depict the chemical structures of 21 compounds selected from high-throughput screening for inhibitors of UL44-UL54 peptide interaction.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

The term "prodrug" is art-recognized and is intended to encompass compounds which, under physiological conditions, are converted into active compounds, e.g., those described herein. A common method for making a prodrug is to select moieties which are hydrolyzed under physiological conditions to provide the desired compound. In other embodiments, the prodrug is converted by an enzymatic activity of the host animal.

The term "structure-activity relationship" or "(SAR)" is art-recognized and refers to the way in which altering the molecular structure of a drug or other compound alters its interaction with a receptor, enzyme, nucleic acid or other target and the like.

The term "aliphatic" is art-recognized and refers to a linear, branched, cyclic alkane, alkene, or alkyne. In certain embodiments, aliphatic groups are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, naphtalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

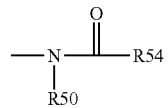

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

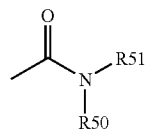

wherein R50 and R51 are as defined above. Certain embodiments of the amide will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carbonyl" is art recognized and includes such moieties as may be represented by the general formulas:

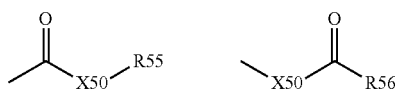

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R61, where m and R61 are described above.

The term "sulfonate" is art recognized and refers to a moiety that may be represented by the general formula:

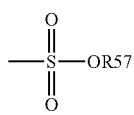

in which R57 is an electron pair, hydrogen, alkyl, cycloalkyl, or aryl.

The term "sulfate" is art recognized and includes a moiety that may be represented by the general formula:

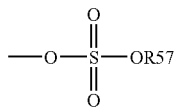

in which R57 is as defined above.

The term "sulfonamido" is art recognized and includes a moiety that may be represented by the general formula:

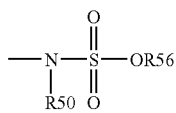

in which R50 and R56 are as defined above.

The term "sulfamoyl" is art-recognized and refers to a moiety that may be represented by the general formula:

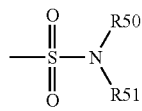

in which R50 and R51 are as defined above.

The term "sulfonyl" is art-recognized and refers to a moiety that may be represented by the general formula:

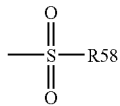

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

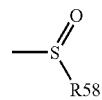

in which R58 is defined above.

The term "phosphoryl" is art-recognized and may in general be represented by the formula:

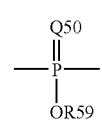

wherein Q50 represents S or O, and R59 represents hydrogen, a lower alkyl or an aryl. When used to substitute, e.g., an alkyl, the phosphoryl group of the phosphorylalkyl may be represented by the general formulas:

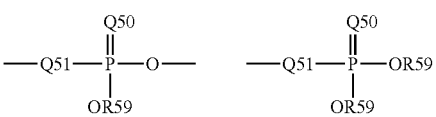

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

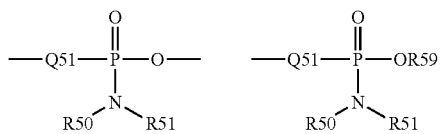

wherein Q51, R50, R51 and R59 are as defined above.

The term "phosphonamidite" is art-recognized and may be represented in the general formulas:

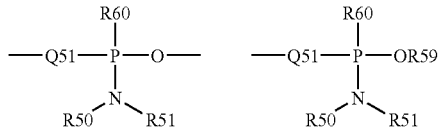

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions described herein may exist in particular geometric or stereoisomeric forms. For example, compositions may include cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. All such isomers, as well as mixtures thereof, are disclosed herein.

If, for instance, a particular enantiomer of a compound described herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. Heteroatoms such as nitrogen may have hydrogen substituents and/or any permissible substituents of organic compounds described herein which satisfy the valences of the heteroatoms. The compounds are not intended to be limited in any manner by the permissible substituents of organic compounds.

The chemical elements are identified in accordance with the Periodic Table of the Elements, CAS version, *Handbook of Chemistry and Physics*, $67^{th}$ Ed., 1986-87, inside cover.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* ($2^{nd}$ ed., Wiley: New York, 1991).

The term "therapeutic agent" is art-recognized and refers to any chemical moiety that is a biologically, physiologically, or pharmacologically active substance that acts locally or systemically in a subject. The term means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a at a reasonable benefit/risk ratio applicable to such treatment.

"Treating" a condition or disease refers to curing as well as ameliorating at least one symptom of any condition or disease.

The terms "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" when referring to a compound is art-recognized and refers to a form of a compound that allows for it, or a portion of the amount of compound administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions described herein.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Exemplary Antiviral Compounds

One antiviral compound has formula 1:

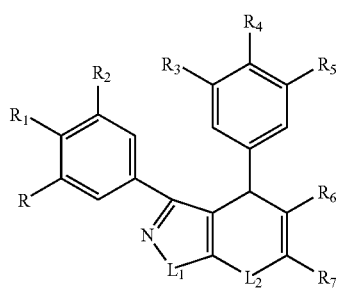

wherein, independently for each occurrence:

R, $R_1$, $R_2$, $R_3$, $R_4$, $R_5$, $R_6$, and $R_7$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$ and $L_2$ are O, $NR_8$, or S; and $R_8$ is H or a substituted or unsubstituted alkyl, aryl, aralkyl, heterocyclyl, heterocyclylalkyl, heteroaryl, or heteroaralkyl.

In a further embodiment, the antiviral compound is a compound of formula 1 and the attendant definitions wherein R is H.

In a further embodiment, the antiviral compound is a compound of formula 1 and the attendant definitions wherein R is OMe.

In a further embodiment, the antiviral compound is a compound of formula 1 and the attendant definitions wherein $R_1$ is H.

In a further embodiment, the antiviral compound is a compound of formula 1 and the attendant definitions wherein $R_1$ is OMe.

In a further embodiment, the antiviral compound is a compound of formula 1 and the attendant definitions wherein $R_1$ is Cl.

In a further embodiment, the antiviral compound is a compound of formula 1 and the attendant definitions wherein $R_2$ is H.

In a further embodiment, the antiviral compound is a compound of formula 1 and the attendant definitions wherein $R_2$ is OMe.

In a further embodiment, the antiviral compound is a compound of formula 1 and the attendant definitions wherein $R_3$ is $NO_2$.

In a further embodiment, the antiviral compound is a compound of formula 1 and the attendant definitions wherein $R_4$ is OH.

In a further embodiment, the antiviral compound is a compound of formula 1 and the attendant definitions wherein $R_5$ is OEt.

In a further embodiment, the antiviral compound is a compound of formula 1 and the attendant definitions wherein $R_6$ is CN.

In a further embodiment, the antiviral compound is a compound of formula 1 and the attendant definitions wherein $R_7$ is $NH_2$.

In a further embodiment, the antiviral compound is a compound of formula 1 and the attendant definitions wherein $L_1$ is O.

In a further embodiment, the antiviral compound is a compound of formula 1 and the attendant definitions wherein $L_2$ is NH.

In a further embodiment, the antiviral compound is a compound of formula 1 and the attendant definitions wherein R is H and $R_1$ is H.

In a further embodiment, the antiviral compound is a compound of formula 1 and the attendant definitions wherein R is H, $R_1$ is H, and $R_2$ is H.

In a further embodiment, the antiviral compound is a compound of formula 1 and the attendant definitions wherein R is H, $R_1$ is H, $R_2$ is H, and $R_3$ is $NO_2$.

In a further embodiment, the antiviral compound is a compound of formula 1 and the attendant definitions wherein R is H, $R_1$ is H, $R_2$ is H, $R_3$ is $NO_2$, and $R_4$ is OH.

In a further embodiment, the antiviral compound is a compound of formula 1 and the attendant definitions wherein R is H, $R_1$ is H, $R_2$ is H, $R_3$ is $NO_2$, $R_4$ is OH, and $R_5$ is OEt.

In a further embodiment, the antiviral compound is a compound of formula 1 and the attendant definitions wherein R is H, $R_1$ is H, $R_2$ is H, $R_3$ is $NO_2$, $R_4$ is OH, $R_5$ is OEt, and $R_6$ is CN.

In a further embodiment, the antiviral compound is a compound of formula 1 and the attendant definitions wherein R is H, $R_1$ is H, $R_2$ is H, $R_3$ is $NO_2$, $R_4$ is OH, $R_5$ is OEt, $R_6$ is CN, and $R_7$ is $NH_2$.

In a further embodiment, the antiviral compound is a compound of formula 1 and the attendant definitions wherein R is H, $R_1$ is H, $R_2$ is H, $R_3$ is $NO_2$, $R_4$ is OH, $R_5$ is OEt, $R_6$ is CN, $R_7$ is $NH_2$, and $L_1$ is NH.

In a further embodiment, the antiviral compound is a compound of formula 1 and the attendant definitions wherein R is H, $R_1$ is H, $R_2$ is H, $R_3$ is $NO_2$, $R_4$ is OH, $R_5$ is OEt, $R_6$ is CN, $R_7$ is $NH_2$, $L_1$ is NH, and $L_2$ is O.

In a further embodiment, the antiviral compound is a compound of formula 1 and the attendant definitions wherein R is H and $R_1$ is OMe.

In a further embodiment, the antiviral compound is a compound of formula 1 and the attendant definitions wherein R is H, $R_1$ is OMe, and $R_2$ is H.

In a further embodiment, the antiviral compound is a compound of formula 1 and the attendant definitions wherein R is H, $R_1$ is OMe, $R_2$ is H, and $R_3$ is $NO_2$.

In a further embodiment, the antiviral compound is a compound of formula 1 and the attendant definitions wherein R is H, $R_1$ is OMe, $R_2$ is H, $R_3$ is $NO_2$, and $R_4$ is OH.

In a further embodiment, the antiviral compound is a compound of formula 1 and the attendant definitions wherein R is H, $R_1$ is OMe, $R_2$ is H, $R_3$ is $NO_2$, $R_4$ is OH, and $R_5$ is OEt.

In a further embodiment, the antiviral compound is a compound of formula 1 and the attendant definitions wherein R is H, $R_1$ is OMe, $R_2$ is H, $R_3$ is $NO_2$, $R_4$ is OH, $R_5$ is OEt, and $R_6$ is CN.

In a further embodiment, the antiviral compound is a compound of formula 1 and the attendant definitions wherein R is H, $R_1$ is OMe, $R_2$ is H, $R_3$ is $NO_2$, $R_4$ is OH, $R_5$ is OEt, $R_6$ is CN, and $R_7$ is $NH_2$.

In a further embodiment, the antiviral compound is a compound of formula 1 and the attendant definitions wherein R is H, $R_1$ is OMe, $R_2$ is H, $R_3$ is $NO_2$, $R_4$ is OH, $R_5$ is OEt, $R_6$ is CN, $R_7$ is $NH_2$, and $L_1$ is NH.

In a further embodiment, the antiviral compound is a compound of formula 1 and the attendant definitions wherein R is H, $R_1$ is OMe, $R_2$ is H, $R_3$ is $NO_2$, $R_4$ is OH, $R_5$ is OEt, $R_6$ is CN, $R_7$ is $NH_2$, $L_1$ is NH, and $L_2$ is O.

In a further embodiment, the antiviral compound is a compound of formula 1 and the attendant definitions wherein R is H and $R_1$ is Cl.

In a further embodiment, the antiviral compound is a compound of formula 1 and the attendant definitions wherein R is H, $R_1$ is Cl, and $R_2$ is H.

In a further embodiment, the antiviral compound is a compound of formula 1 and the attendant definitions wherein R is H, $R_1$ is Cl, $R_2$ is H, and $R_3$ is $NO_2$.

In a further embodiment, the antiviral compound is a compound of formula 1 and the attendant definitions wherein R is H, $R_1$ is Cl, $R_2$ is H, $R_3$ is $NO_2$, and $R_4$ is OH.

In a further embodiment, the antiviral compound is a compound of formula 1 and the attendant definitions wherein R is H, $R_1$ is Cl, $R_2$ is H, $R_3$ is $NO_2$, $R_4$ is OH, and $R_5$ is OEt.

In a further embodiment, the antiviral compound is a compound of formula 1 and the attendant definitions wherein R is H, $R_1$ is Cl, $R_2$ is H, $R_3$ is $NO_2$, $R_4$ is OH, $R_5$ is OEt, and $R_6$ is CN.

In a further embodiment, the antiviral compound is a compound of formula 1 and the attendant definitions wherein R is H, $R_1$ is Cl, $R_2$ is H, $R_3$ is $NO_2$, $R_4$ is OH, $R_5$ is OEt, $R_6$ is CN, and $R_7$ is $NH_2$.

In a further embodiment, the antiviral compound is a compound of formula 1 and the attendant definitions wherein R is H, $R_1$ is Cl, $R_2$ is H, $R_3$ is $NO_2$, $R_4$ is OH, $R_5$ is OEt, $R_6$ is CN, $R_7$ is $NH_2$, and $L_1$ is NH.

In a further embodiment, the antiviral compound is a compound of formula 1 and the attendant definitions wherein R is H, $R_1$ is Cl, $R_2$ is H, $R_3$ is $NO_2$, $R_4$ is OH, $R_5$ is OEt, $R_6$ is CN, $R_7$ is $NH_2$, $L_1$ is NH, and $L_2$ is O.

In a further embodiment, the antiviral compound is a compound of formula 1 and the attendant definitions wherein R is OMe and $R_1$ is OMe.

In a further embodiment, the antiviral compound is a compound of formula 1 and the attendant definitions wherein R is OMe, $R_1$ is OMe, and $R_2$ is OMe.

In a further embodiment, the antiviral compound is a compound of formula 1 and the attendant definitions wherein R is OMe, $R_1$ is OMe, $R_2$ is OMe, and $R_3$ is $NO_2$.

In a further embodiment, the antiviral compound is a compound of formula 1 and the attendant definitions wherein R is OMe, $R_1$ is OMe, $R_2$ is OMe, $R_3$ is $NO_2$, and $R_4$ is OH.

In a further embodiment, the antiviral compound is a compound of formula 1 and the attendant definitions wherein R is OMe, $R_1$ is OMe, $R_2$ is OMe, $R_3$ is $NO_2$, $R_4$ is OH, and $R_5$ is OEt.

In a further embodiment, the antiviral compound is a compound of formula 1 and the attendant definitions wherein R is OMe, $R_1$ is OMe, $R_2$ is OMe, $R_3$ is $NO_2$, $R_4$ is OH, $R_5$ is OEt, and $R_6$ is CN.

In a further embodiment, the antiviral compound is a compound of formula 1 and the attendant definitions wherein R is OMe, $R_1$ is OMe, $R_2$ is OMe, $R_3$ is $NO_2$, $R_4$ is OH, $R_5$ is OEt, $R_6$ is CN, and $R_7$ is $NH_2$.

In a further embodiment, the antiviral compound is a compound of formula 1 and the attendant definitions wherein R is OMe, $R_1$ is OMe, $R_2$ is OMe, $R_3$ is $NO_2$, $R_4$ is OH, $R_5$ is OEt, $R_6$ is CN, $R_7$ is $NH_2$, and $L_1$ is NH.

In a further embodiment, the antiviral compound is a compound of formula 1 and the attendant definitions wherein R is OMe, $R_1$ is OMe, $R_2$ is OMe, $R_3$ is $NO_2$, $R_4$ is OH, $R_5$ is OEt, $R_6$ is CN, $R_7$ is $NH_2$, $L_1$ is NH, and $L_2$ is O.

Exemplary compounds having formula 1 are compounds 1, 2, 3 and 4 set forth in FIG. 1a.

Another antiviral compound is a compound of formula 2:

wherein, independently for each occurrence:

R and $R_2$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ is H or a substituted or unsubstituted alkyl, aryl, aralkyl, heterocyclyl, heterocyclylalkyl, heteroaryl, or heteroaralkyl;

$R_3$ is a heterocyclic;

n is an integer from 0 to 4 inclusive; and m is an integer from 0 to 2 inclusive.

In a further embodiment, the antiviral compound is a compound of formula 2 and the attendant definitions wherein n is 0.

In a further embodiment, the antiviral compound is a compound of formula 2 and the attendant definitions wherein m is 0.

In a further embodiment, the antiviral compound is a compound of formula 2 and the attendant definitions wherein $R_1$ is methyl.

In a further embodiment, the antiviral compound is a compound of formula 2 and the attendant definitions wherein $R_3$ is N-1-piperidyl.

In a further embodiment, the antiviral compound is a compound of formula 2 and the attendant definitions wherein n is 0 and m is 0.

In a further embodiment, the antiviral compound is a compound of formula 2 and the attendant definitions wherein n is 0, m is 0, and $R_1$ is methyl.

In a further embodiment, the antiviral compound is a compound of formula 2 and the attendant definitions wherein n is 0, m is 0, $R_1$ is methyl, and $R_3$ is N-1-piperidyl.

An exemplary compound having formula 2 is compound 5 set forth in FIG. 1a.

Another antiviral compound is a compound of formula 3:

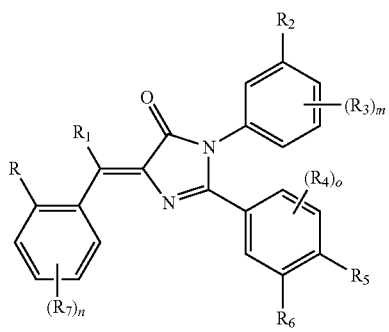

3 wherein, independently for each occurrence:

R, $R_2$, $R_3$, $R_4$, $R_5$, $R_6$, and $R_7$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ is H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

m and n are integers from 0 to 4 inclusive; and o is an integer from 0 to 3 inclusive In a further embodiment, the antiviral compound is a compound of formula 3 and the attendant definitions wherein R is OMe.

In a further embodiment, the antiviral compound is a compound of formula 3 and the attendant definitions wherein $R_1$ is H.

In a further embodiment, the antiviral compound is a compound of formula 3 and the attendant definitions wherein $R_2$ is F.

In a further embodiment, the antiviral compound is a compound of formula 3 and the attendant definitions wherein m is 0.

In a further embodiment, the antiviral compound is a compound of formula 3 and the attendant definitions wherein o is 0.

In a further embodiment, the antiviral compound is a compound of formula 3 and the attendant definitions wherein $R_5$ is OMe.

In a further embodiment, the antiviral compound is a compound of formula 3 and the attendant definitions wherein $R_6$ is OMe.

In a further embodiment, the antiviral compound is a compound of formula 3 and the attendant definitions wherein n is 0.

In a further embodiment, the antiviral compound is a compound of formula 3 and the attendant definitions wherein R is OMe and $R_1$ is H.

In a further embodiment, the antiviral compound is a compound of formula 3 and the attendant definitions wherein R is OMe, $R_1$ is H, and $R_2$ is F.

In a further embodiment, the antiviral compound is a compound of formula 3 and the attendant definitions wherein R is OMe, $R_1$ is H, $R_2$ is F, and m is 0.

In a further embodiment, the antiviral compound is a compound of formula 3 and the attendant definitions wherein R is OMe, $R_1$ is H, $R_2$ is F, m is 0, and o is 0.

In a further embodiment, the antiviral compound is a compound of formula 3 and the attendant definitions wherein R is OMe, $R_1$ is H, $R_2$ is F, m is 0, o is 0, and $R_5$ is OMe.

In a further embodiment, the antiviral compound is a compound of formula 3 and the attendant definitions wherein R is OMe, $R_1$ is H, $R_2$ is F, m is 0, o is 0, $R_5$ is OMe, and $R_6$ is OMe.

In a further embodiment, the antiviral compound is a compound of formula 3 and the attendant definitions wherein R is OMe, $R_1$ is H, $R_2$ is F, m is 0, o is 0, $R_5$ is OMe, $R_6$ is OMe, and n is 0.

An exemplary compound having formula 3 is compound 6 set forth in FIG. 1a.

An antiviral may also be a compound of formula 4:

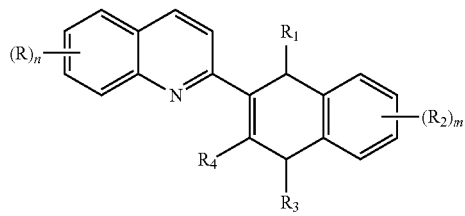

4 wherein, independently for each occurrence:

R and $R_2$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$, $R_3$, and $R_4$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

n is an integer from 0 to 6 inclusive; and m is an integer from 0 to 4 inclusive.

In a further embodiment, the antiviral compound is a compound of formula 4 and the attendant definitions wherein n is 0.

In a further embodiment, the antiviral compound is a compound of formula 4 and the attendant definitions wherein m is 0.

In a further embodiment, the antiviral compound is a compound of formula 4 and the attendant definitions wherein $R_1$ is CN.

In a further embodiment, the antiviral compound is a compound of formula 4 and the attendant definitions wherein $R_3$ is methyl.

In a further embodiment, the antiviral compound is a compound of formula 4 and the attendant definitions wherein $R_4$ is H.

In a further embodiment, the antiviral compound is a compound of formula 4 and the attendant definitions wherein n is 0 and m is 0.

In a further embodiment, the antiviral compound is a compound of formula 4 and the attendant definitions wherein n is 0, m is 0, and $R_1$ is CN.

In a further embodiment, the antiviral compound is a compound of formula 4 and the attendant definitions wherein n is 0, m is 0, $R_1$ is CN, and $R_3$ is methyl.

In a further embodiment, the antiviral compound is a compound of formula 4 and the attendant definitions wherein n is 0, m is 0, $R_1$ is CN, $R_3$ is methyl, and $R_4$ is H.

An exemplary compound having formula 4 is compound 7 set forth in FIG. 1a.

An antiviral compound may be a compound of formula 5:

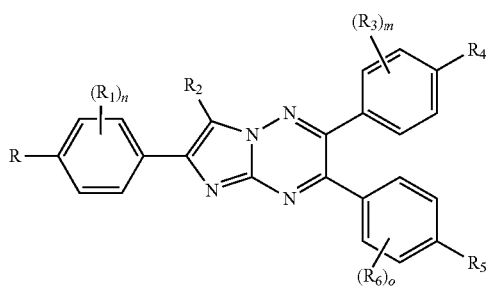

5 wherein, independently for each occurrence:

R, $R_2$, $R_4$, and $R_5$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$, $R_3$, and $R_5$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl; and n, m, an o are integers from 0 to 4 inclusive.

In a further embodiment, the antiviral compound is a compound of formula 5 and the attendant definitions wherein R is Br.

In a further embodiment, the antiviral compound is a compound of formula 5 and the attendant definitions wherein n is 0.

In a further embodiment, the antiviral compound is a compound of formula 5 and the attendant definitions wherein $R_2$ is H.

In a further embodiment, the antiviral compound is a compound of formula 5 and the attendant definitions wherein m is 0.

In a further embodiment, the antiviral compound is a compound of formula 5 and the attendant definitions wherein $R_4$ is methyl.

In a further embodiment, the antiviral compound is a compound of formula 5 and the attendant definitions wherein o is 0.

In a further embodiment, the antiviral compound is a compound of formula 5 and the attendant definitions wherein $R_5$ is methyl.

In a further embodiment, the antiviral compound is a compound of formula 5 and the attendant definitions wherein R is Br and n is 0.

In a further embodiment, the antiviral compound is a compound of formula 5 and the attendant definitions wherein R is Br, n is 0, and $R_2$ is H.

In a further embodiment, the antiviral compound is a compound of formula 5 and the attendant definitions wherein R is Br, n is 0, $R_2$ is H, and m is 0.

In a further embodiment, the antiviral compound is a compound of formula 5 and the attendant definitions wherein R is Br, n is 0, $R_2$ is H, m is 0, and $R_4$ is methyl.

In a further embodiment, the antiviral compound is a compound of formula 5 and the attendant definitions wherein R is Br, n is 0, $R_2$ is H, m is 0, $R_4$ is methyl, and o is 0.

In a further embodiment, the antiviral compound is a compound of formula 5 and the attendant definitions wherein R is Br, n is 0, $R_2$ is H, m is 0, $R_4$ is methyl, o is 0, and $R_5$ is methyl.

An exemplary compound having formula 5 is compound 8 set forth in FIG. 1a.

An antiviral compound may also be a compound of formula 6:

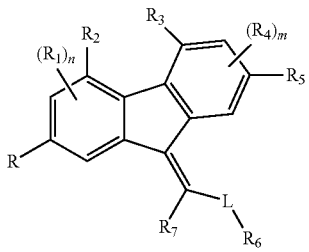

6 wherein, independently for each occurrence:

R, $R_2$, $R_3$, $R_5$, and $R_7$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_4$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_6$ is H, carbonyl, or a substituted or unsubstituted alkyl, aryl, aralkyl, heterocyclyl, heterocyclylalkyl, heteroaryl, or heteroaralkyl;

L is O, $NR_6$, or S; and n and m are 0, 1, or 2.

In a further embodiment, the antiviral compound is a compound of formula 6 and the attendant definitions wherein R is $NO_2$.

In a further embodiment, the antiviral compound is a compound of formula 6 and the attendant definitions wherein n is 0.

In a further embodiment, the antiviral compound is a compound of formula 6 and the attendant definitions wherein $R_2$ is $NO_2$.

In a further embodiment, the antiviral compound is a compound of formula 6 and the attendant definitions wherein $R_3$ is $NO_2$.

In a further embodiment, the antiviral compound is a compound of formula 6 and the attendant definitions wherein m is 0.

In a further embodiment, the antiviral compound is a compound of formula 6 and the attendant definitions wherein $R_5$ is $NO_2$.

In a further embodiment, the antiviral compound is a compound of formula 6 and the attendant definitions wherein $R_6$ is propyl.

In a further embodiment, the antiviral compound is a compound of formula 6 and the attendant definitions wherein $R_7$ is H.

In a further embodiment, the antiviral compound is a compound of formula 6 and the attendant definitions wherein L is O.

In a further embodiment, the antiviral compound is a compound of formula 6 and the attendant definitions wherein R is $NO_2$ and n is 0.

In a further embodiment, the antiviral compound is a compound of formula 6 and the attendant definitions wherein R is $NO_2$, n is 0, and $R_2$ is $NO_2$.

In a further embodiment, the antiviral compound is a compound of formula 6 and the attendant definitions wherein R is $NO_2$, n is 0, $R_2$ is $NO_2$, and $R_3$ is $NO_2$.

In a further embodiment, the antiviral compound is a compound of formula 6 and the attendant definitions wherein R is $NO_2$, n is 0, $R_2$ is $NO_2$, $R_3$ is $NO_2$, and m is 0.

In a further embodiment, the antiviral compound is a compound of formula 6 and the attendant definitions wherein R is $NO_2$, n is 0, $R_2$ is $NO_2$, $R_3$ is $NO_2$, m is 0, and $R_5$ is $NO_2$.

In a further embodiment, the antiviral compound is a compound of formula 6 and the attendant definitions wherein R is $NO_2$, n is 0, $R_2$ is $NO_2$, $R_3$ is $NO_2$, m is 0, $R_5$ is $NO_2$, and $R_6$ is propyl.

In a further embodiment, the antiviral compound is a compound of formula 6 and the attendant definitions wherein R is $NO_2$, n is 0, $R_2$ is $NO_2$, $R_3$ is $NO_2$, m is 0, $R_5$ is $NO_2$, $R_6$ is propyl, and $R_7$ is H.

In a further embodiment, the antiviral compound is a compound of formula 6 and the attendant definitions wherein R is $NO_2$, n is 0, $R_2$ is $NO_2$, $R_3$ is $NO_2$, m is 0, $R_5$ is $NO_2$, $R_6$ is propyl, $R_7$ is H, and L is O.

An exemplary compound having formula 6 is compound 9 set forth in FIG. 1a.

An antiviral compound may also be a compound of formula 7:

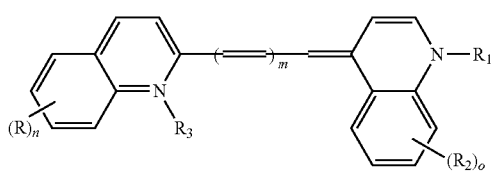

7 wherein, independently for each occurrence:

R and $R_2$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_3$ are H, carbonyl, or a substituted or unsubstituted alkyl, aryl, aralkyl, heterocyclyl, heterocyclylalkyl, heteroaryl, or heteroaralkyl;

n is an integer from 0 to 6 inclusive;

m is an integer from 1 to 3 inclusive; and o is an integer from 0 to 6 inclusive.

In a further embodiment, the antiviral compound is a compound of formula 7 and the attendant definitions wherein n is 0.

In a further embodiment, the antiviral compound is a compound of formula 7 and the attendant definitions wherein m is 1.

In a further embodiment, the antiviral compound is a compound of formula 7 and the attendant definitions wherein $R_1$ is ethyl.

In a further embodiment, the antiviral compound is a compound of formula 7 and the attendant definitions wherein o is 0.

In a further embodiment, the antiviral compound is a compound of formula 7 and the attendant definitions wherein $R_3$ is ethyl.

In a further embodiment, the antiviral compound is a compound of formula 7 and the attendant definitions wherein n is 0 and m is 1.

In a further embodiment, the antiviral compound is a compound of formula 7 and the attendant definitions wherein n is 0, m is 1, and $R_1$ is ethyl.

In a further embodiment, the antiviral compound is a compound of formula 7 and the attendant definitions wherein n is 0, m is 1, $R_1$ is ethyl, and o is 0.

In a further embodiment, the antiviral compound is a compound of formula 7 and the attendant definitions wherein n is 0, m is 1, $R_1$ is ethyl, o is 0, and $R_3$ is ethyl.

An exemplary compound having formula 7 is compound 10 set forth in FIG. 1a.

An antiviral compound may also be a compound of formula 8:

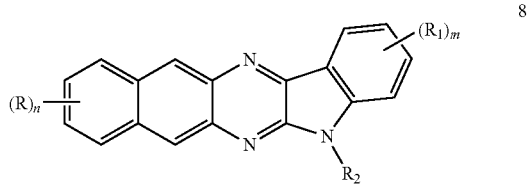

8 wherein, independently for each occurrence:

R and $R_1$ is hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is H, carbonyl, or a substituted or unsubstituted alkyl, aryl, aralkyl, heterocyclyl, heterocyclylalkyl, heteroaryl, or heteroaralkyl;

n is an integer from 0 to 6 inclusive; and m is an integer from 0 to 4 inclusive.

In a further embodiment, the antiviral compound is a compound of formula 8 and the attendant definitions wherein n is 0.

In a further embodiment, the antiviral compound is a compound of formula 8 and the attendant definitions wherein m is 0.

In a further embodiment, the antiviral compound is a compound of formula 8 and the attendant definitions wherein $R_2$ is ethyl.

In a further embodiment, the antiviral compound is a compound of formula 8 and the attendant definitions wherein n is 0 and m is 0.

In a further embodiment, the antiviral compound is a compound of formula 8 and the attendant definitions wherein n is 0, m is 0, and $R_2$ is ethyl.

An exemplary compound having formula 8 is compound 11 set forth in FIG. 1a.

An antiviral compound may also be a compound of formula 9:

9 wherein, independently for each occurrence:
R and $R_1$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
n is an integer from 0 to 6 inclusive; and
m is an integer from 0 to 4 inclusive.

In a further embodiment, the antiviral compound is a compound of formula 9 and the attendant definitions wherein n is 0.

In a further embodiment, the antiviral compound is a compound of formula 9 and the attendant definitions wherein m is 0.

In a further embodiment, the antiviral compound is a compound of formula 9 and the attendant definitions wherein n is 0 and m is 0.

Figure 1B:
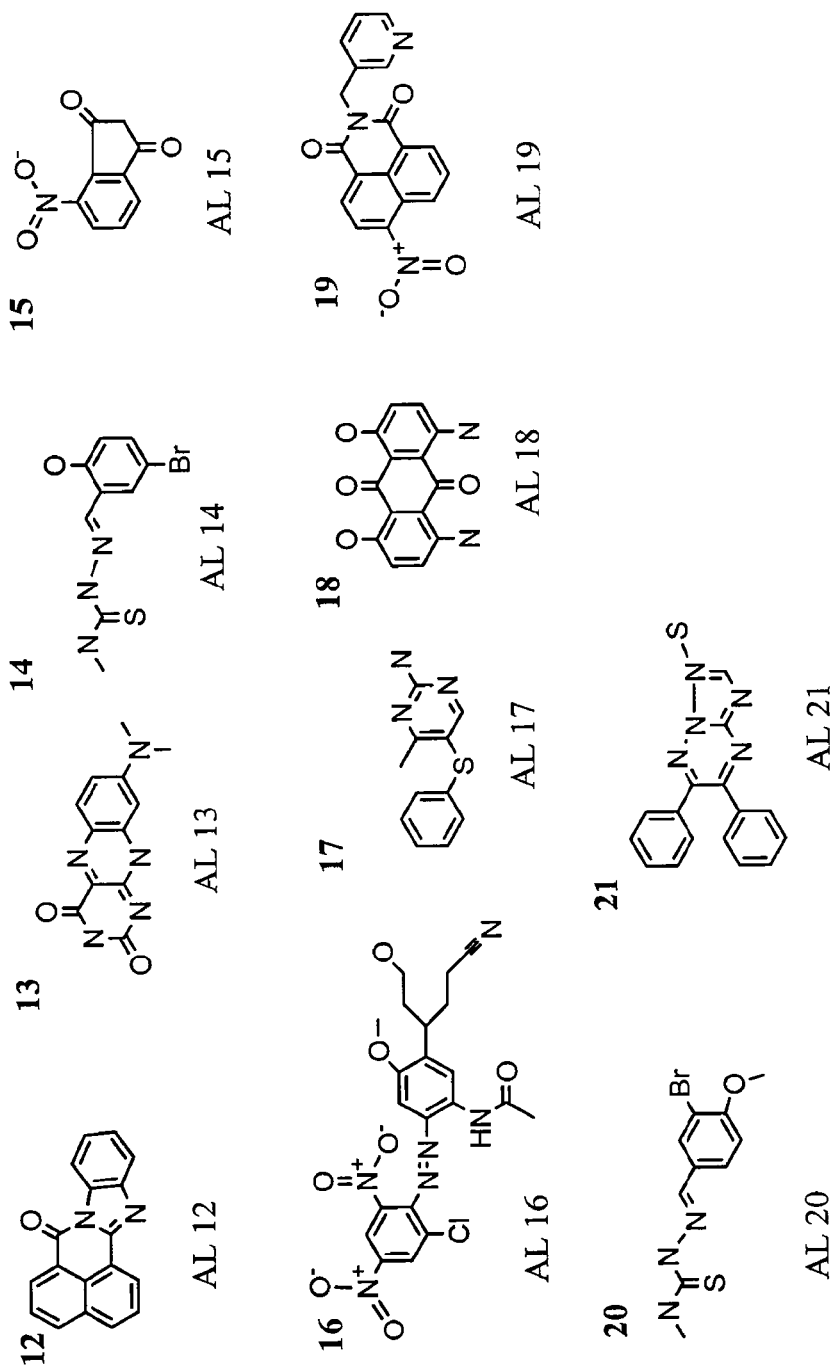

An exemplary compound having formula 9 is compound 12 set forth in FIG. 1b.

An antiviral compound may also be a compound of formula 10:

10 wherein, independently for each occurrence:
R is hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
$R_1$ and $R_2$ are H, carbonyl, or a substituted or unsubstituted alkyl, aryl, aralkyl, heterocyclyl, heterocyclylalkyl, heteroaryl, or heteroaralkyl;
$L_1$ and $L_2$ are O, $NR_1$, or S; and
n is an integer from 0 to 3 inclusive.

In a further embodiment, the antiviral compound is a compound of formula 10 and the attendant definitions wherein n is 0.

In a further embodiment, the antiviral compound is a compound of formula 10 and the attendant definitions wherein $R_1$ is methyl.

In a further embodiment, the antiviral compound is a compound of formula 10 and the attendant definitions wherein $R_2$ is methyl.

In a further embodiment, the antiviral compound is a compound of formula 10 and the attendant definitions wherein $L_1$ is NH.

In a further embodiment, the antiviral compound is a compound of formula 10 and the attendant definitions wherein $L_2$ is NH.

In a further embodiment, the antiviral compound is a compound of formula 10 and the attendant definitions wherein n is 0 and $R_1$ is methyl.

In a further embodiment, the antiviral compound is a compound of formula 10 and the attendant definitions wherein n is 0, $R_1$ is methyl, and $R_2$ is methyl.

In a further embodiment, the antiviral compound is a compound of formula 10 and the attendant definitions wherein n is 0, $R_1$ is methyl, $R_2$ is methyl, and $L_1$ is NH.

In a further embodiment, the antiviral compound is a compound of formula 10 and the attendant definitions wherein n is 0, $R_1$ is methyl, $R_2$ is methyl, $L_1$ is NH, and $L_2$ is NH.

An exemplary compound having formula 10 is compound 13 set forth in FIG. 1b.

An antiviral compound may also be a compound of formula 11:

11 wherein, independently for each occurrence:
R, $R_1$, and $R_2$ are H, carbonyl, or a substituted or unsubstituted alkyl, aryl, aralkyl, heterocyclyl, heterocyclylalkyl, heteroaryl, or heteroaralkyl; and
$R_3$, $R_4$, $R_5$, $R_6$, and $R_7$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl.

In a further embodiment, the antiviral compound is a compound of formula 11 and the attendant definitions wherein R is methyl.

In a further embodiment, the antiviral compound is a compound of formula 11 and the attendant definitions wherein $R_1$ is H.

In a further embodiment, the antiviral compound is a compound of formula 11 and the attendant definitions wherein $R_2$ is H.

In a further embodiment, the antiviral compound is a compound of formula 11 and the attendant definitions wherein $R_3$ is H.

In a further embodiment, the antiviral compound is a compound of formula 11 and the attendant definitions wherein $R_4$ is H.

In a further embodiment, the antiviral compound is a compound of formula 11 and the attendant definitions wherein $R_4$ is OH.

In a further embodiment, the antiviral compound is a compound of formula 11 and the attendant definitions wherein $R_5$ is H.

In a further embodiment, the antiviral compound is a compound of formula 11 and the attendant definitions wherein $R_5$ is Br.

In a further embodiment, the antiviral compound is a compound of formula 11 and the attendant definitions wherein $R_6$ is H.

In a further embodiment, the antiviral compound is a compound of formula 11 and the attendant definitions wherein $R_6$ is OMe.

In a further embodiment, the antiviral compound is a compound of formula 11 and the attendant definitions wherein $R_7$ is H.

In a further embodiment, the antiviral compound is a compound of formula 11 and the attendant definitions wherein $R_7$ is Br.

In a further embodiment, the antiviral compound is a compound of formula 11 and the attendant definitions wherein R is methyl and $R_1$ is H.

In a further embodiment, the antiviral compound is a compound of formula 11 and the attendant definitions wherein R is methyl, $R_1$ is H, and $R_2$ is H.

In a further embodiment, the antiviral compound is a compound of formula 11 and the attendant definitions wherein R is methyl, $R_1$ is H, $R_2$ is H, and $R_3$ is H.

In a further embodiment, the antiviral compound is a compound of formula 11 and the attendant definitions wherein R is methyl, $R_1$ is H, $R_2$ is H, $R_3$ is H, and $R_4$ is OH.

In a further embodiment, the antiviral compound is a compound of formula 11 and the attendant definitions wherein R is methyl, $R_1$ is H, $R_2$ is H, $R_3$ is H, $R_4$ is OH, and $R_5$ is H.

In a further embodiment, the antiviral compound is a compound of formula 11 and the attendant definitions wherein R is methyl, $R_1$ is H, $R_2$ is H, $R_3$ is H, $R_4$ is OH, $R_5$ is H, and $R_6$ is H.

In a further embodiment, the antiviral compound is a compound of formula 11 and the attendant definitions wherein R is methyl, $R_1$ is H, $R_2$ is H, $R_3$ is H, $R_4$ is OH, $R_5$ is H, $R_6$ is H, and $R_7$ is Br.

In a further embodiment, the antiviral compound is a compound of formula 11 and the attendant definitions wherein R is methyl, $R_1$ is H, $R_2$ is H, $R_3$ is H, and $R_4$ is H.

In a further embodiment, the antiviral compound is a compound of formula 11 and the attendant definitions wherein R is methyl, $R_1$ is H, $R_2$ is H, $R_3$ is H, $R_4$ is H, and $R_5$ is Br.

In a further embodiment, the antiviral compound is a compound of formula 11 and the attendant definitions wherein R is methyl, $R_1$ is H, $R_2$ is H, $R_3$ is H, $R_4$ is H, $R_5$ is Br, and $R_6$ is OMe.

In a further embodiment, the antiviral compound is a compound of formula 11 and the attendant definitions wherein R is methyl, $R_1$ is H, $R_2$ is H, $R_3$ is H, $R_4$ is H, $R_5$ is Br, $R_6$ is OMe, and $R_7$ is H.

Exemplary compounds having formula 11 are compounds 14 and 20 set forth in FIG. 1b.

An antiviral compound may also be a compound of formula 12:

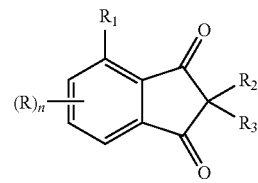

wherein, independently for each occurrence:

R and $R_1$, are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ and $R_3$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl; and n is an integer from 0 to 3 inclusive.

In a further embodiment, the antiviral compound is a compound of formula 12 and the attendant definitions wherein n is 0.

In a further embodiment, the antiviral compound is a compound of formula 12 and the attendant definitions wherein $R_1$ is $NO_2$.

In a further embodiment, the antiviral compound is a compound of formula 12 and the attendant definitions wherein $R_2$ is H.

In a further embodiment, the antiviral compound is a compound of formula 12 and the attendant definitions wherein $R_3$ is H.

In a further embodiment, the antiviral compound is a compound of formula 12 and the attendant definitions wherein n is 0 and $R_1$ is $NO_2$.

In a further embodiment, the antiviral compound is a compound of formula 12 and the attendant definitions wherein n is 0, $R_1$ is $NO_2$, and $R_2$ is H.

In a further embodiment, the antiviral compound is a compound of formula 12 and the attendant definitions wherein n is 0, $R_1$ is $NO_2$, $R_2$ is H, and $R_3$ is H.

An exemplary compound having formula 12 is compound 15 set forth in FIG. 1b.

An antiviral compound may also be a compound of formula 13:

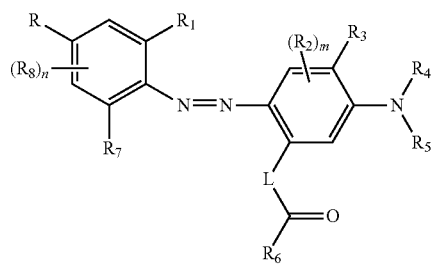

wherein, independently for each occurrence:

R, $R_1$, $R_2$, $R_3$, $R_7$, and R8 are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_4$ and $R_5$ are H, carbonyl, or a substituted or unsubstituted alkyl, aryl, aralkyl, heterocyclyl, heterocyclylalkyl, heteroaryl, or heteroaralkyl;

$R_6$ is H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

L is O, $NR_4$, or S; and m and n are integers from 0 to 2 inclusive.

In a further embodiment, the antiviral compound is a compound of formula 13 and the attendant definitions wherein R is $NO_2$.

In a further embodiment, the antiviral compound is a compound of formula 13 and the attendant definitions wherein $R_1$ is $NO_2$.

In a further embodiment, the antiviral compound is a compound of formula 13 and the attendant definitions wherein n is 0.

In a further embodiment, the antiviral compound is a compound of formula 13 and the attendant definitions wherein $R_3$ is OMe.

In a further embodiment, the antiviral compound is a compound of formula 13 and the attendant definitions wherein $R_4$ is $CH_2CH_2OH$.

In a further embodiment, the antiviral compound is a compound of formula 13 and the attendant definitions wherein $R_5$ is $CH_2CH_2CN$.

In a further embodiment, the antiviral compound is a compound of formula 13 and the attendant definitions wherein $R_6$ is methyl.

In a further embodiment, the antiviral compound is a compound of formula 13 and the attendant definitions wherein $R_7$ is Cl.

In a further embodiment, the antiviral compound is a compound of formula 13 and the attendant definitions wherein n is 0.

In a further embodiment, the antiviral compound is a compound of formula 13 and the attendant definitions wherein L is NH.

In a further embodiment, the antiviral compound is a compound of formula 13 and the attendant definitions wherein R is $NO_2$ and $R_1$ is $NO_2$.

In a further embodiment, the antiviral compound is a compound of formula 13 and the attendant definitions wherein R is $NO_2$, $R_1$ is $NO_2$, and m is 0.

In a further embodiment, the antiviral compound is a compound of formula 13 and the attendant definitions wherein R is $NO_2$, $R_1$ is $NO_2$, m is 0, and $R_3$ is OMe.

In a further embodiment, the antiviral compound is a compound of formula 13 and the attendant definitions wherein R is $NO_2$, $R_1$ is $NO_2$, m is 0, $R_3$ is OMe, and $R_4$ is $CH_2CH_2OH$.

In a further embodiment, the antiviral compound is a compound of formula 13 and the attendant definitions wherein R is $NO_2$, $R_1$ is $NO_2$, m is 0, $R_3$ is OMe, $R_4$ is $CH_2CH_2OH$, and $R_5$ is $CH_2CH_2CN$.

In a further embodiment, the antiviral compound is a compound of formula 13 and the attendant definitions wherein R is $NO_2$, $R_1$ is $NO_2$, m is 0, $R_3$ is OMe, $R_4$ is $CH_2CH_2OH$, $R_5$ is $CH_2CH_2CN$, and $R_6$ is methyl.

In a further embodiment, the antiviral compound is a compound of formula 13 and the attendant definitions wherein R is $NO_2$, $R_1$ is $NO_2$, m is 0, $R_3$ is OMe, $R_4$ is $CH_2CH_2OH$, $R_5$ is $CH_2CH_2CN$, $R_6$ is methyl, and $R_7$ is Cl.

In a further embodiment, the antiviral compound is a compound of formula 13 and the attendant definitions wherein R is $NO_2$, $R_1$ is $NO_2$, m is 0, $R_3$ is OMe, $R_4$ is $CH_2CH_2OH$, $R_5$ is $CH_2CH_2CN$, $R_6$ is methyl, $R_7$ is Cl, and n is 0.

In a further embodiment, the antiviral compound is a compound of formula 13 and the attendant definitions wherein R is $NO_2$, $R_1$ is $NO_2$, m is 0, $R_3$ is OMe, $R_4$ is $CH_2CH_2OH$, $R_5$ is $CH_2CH_2CN$, $R_6$ is methyl, $R_7$ is Cl, n is 0, and L is NH.

An exemplary compound having formula 13 is compound 16 set forth in FIG. 1b.

An antiviral compound may also be a compound of formula 14:

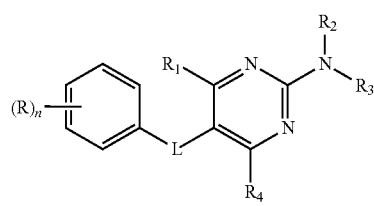

wherein, independently for each occurrence:

R, $R_1$, and $R_4$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ and $R_3$ is H, carbonyl, or a substituted or unsubstituted alkyl, aryl, aralkyl, heterocyclyl, heterocyclylalkyl, heteroaryl, or heteroaralkyl;

L is O, $NR_2$, or S; and n is an integer from 0 to 5 inclusive.

In a further embodiment, the antiviral compound is a compound of formula 14 and the attendant definitions wherein n is 0.

In a further embodiment, the antiviral compound is a compound of formula 14 and the attendant definitions wherein $R_1$ is methyl.

In a further embodiment, the antiviral compound is a compound of formula 14 and the attendant definitions wherein $R_2$ is H.

In a further embodiment, the antiviral compound is a compound of formula 14 and the attendant definitions wherein $R_3$ is H.

In a further embodiment, the antiviral compound is a compound of formula 14 and the attendant definitions wherein $R_4$ is H.

In a further embodiment, the antiviral compound is a compound of formula 14 and the attendant definitions wherein L is S.

In a further embodiment, the antiviral compound is a compound of formula 14 and the attendant definitions wherein n is 0 and $R_1$ is methyl.

In a further embodiment, the antiviral compound is a compound of formula 14 and the attendant definitions wherein n is 0, $R_1$ is methyl, and $R_2$ is H.

In a further embodiment, the antiviral compound is a compound of formula 14 and the attendant definitions wherein n is 0, $R_1$ is methyl, $R_2$ is H, and $R_3$ is H.

In a further embodiment, the antiviral compound is a compound of formula 14 and the attendant definitions wherein n is 0, $R_1$ is methyl, $R_2$ is H, $R_3$ is H, and $R_4$ is H.

In a further embodiment, the antiviral compound is a compound of formula 14 and the attendant definitions wherein n is 0, $R_1$ is methyl, $R_2$ is H, $R_3$ is H, $R_4$ is H, and L is S.

An exemplary compound having formula 14 is compound 17 set forth in FIG. 1b.

An antiviral compound may also be a compound of formula 15:

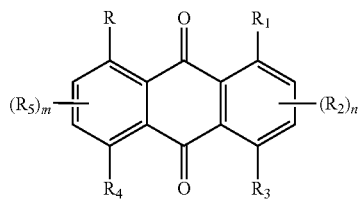

wherein, independently for each occurrence:

R, $R_1$, $R_2$, $R_3$, $R_4$, and $R_5$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl; and m and n are 0, 1, or 2.

In a further embodiment, the antiviral compound is a compound of formula 15 and the attendant definitions wherein R is OH.

In a further embodiment, the antiviral compound is a compound of formula 15 and the attendant definitions wherein $R_1$ is OH.

In a further embodiment, the antiviral compound is a compound of formula 15 and the attendant definitions wherein $R_2$ is NH2.

In a further embodiment, the antiviral compound is a compound of formula 15 and the attendant definitions wherein $R_3$ is NH2.

In a further embodiment, the antiviral compound is a compound of formula 15 and the attendant definitions wherein n is 0.

In a further embodiment, the antiviral compound is a compound of formula 15 and the attendant definitions wherein m is 0.

In a further embodiment, the antiviral compound is a compound of formula 15 and the attendant definitions wherein R is OH and $R_1$ is OH.

In a further embodiment, the antiviral compound is a compound of formula 15 and the attendant definitions wherein R is OH, $R_1$ is OH, and $R_2$ is NH2.

In a further embodiment, the antiviral compound is a compound of formula 15 and the attendant definitions wherein R is OH, $R_1$ is OH, $R_2$ is NH2, and $R_3$ is NH2.

In a further embodiment, the antiviral compound is a compound of formula 15 and the attendant definitions wherein R is OH, $R_1$ is OH, $R_2$ is NH2, $R_3$ is NH2, and n is 0.

In a further embodiment, the antiviral compound is a compound of formula 15 and the attendant definitions wherein R is OH, $R_1$ is OH, $R_2$ is NH2, $R_3$ is NH2, n is 0, and m is 0.

An exemplary compound having formula 15 is compound 18 set forth in FIG. 1b.

An antiviral compound may also be a compound of formula 16:

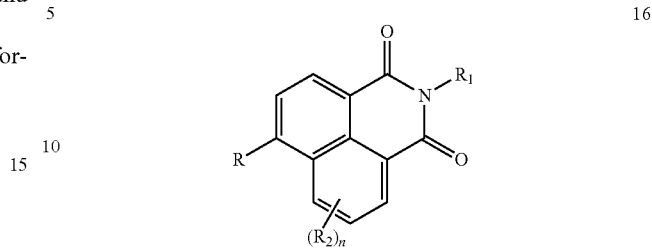

wherein, independently for each occurrence:

R and $R_2$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ is H, carbonyl, or a substituted or unsubstituted alkyl, aryl, aralkyl, heterocyclyl, heterocyclylalkyl, heteroaryl, or heteroaralkyl; and n is an integer from 0 to 5 inclusive.

In a further embodiment, the antiviral compound is a compound of formula 16 and the attendant definitions wherein R is $NO_2$.

In a further embodiment, the antiviral compound is a compound of formula 16 and the attendant definitions wherein $R_1$ is heteroaralkyl.

In a further embodiment, the antiviral compound is a compound of formula 16 and the attendant definitions wherein $R_1$ is $CH_2$-pyridyl.

In a further embodiment, the antiviral compound is a compound of formula 16 and the attendant definitions wherein n is 0.

In a further embodiment, the antiviral compound is a compound of formula 16 and the attendant definitions wherein R is $NO_2$ and $R_1$ is $CH_2$-pyridyl.

In a further embodiment, the antiviral compound is a compound of formula 16 and the attendant definitions wherein R is $NO_2$, $R_1$ is $CH_2$-pyridyl, and n is 0.

An exemplary compound having formula 16 is compound 19 set forth in FIG. 1b.

An antiviral compound may also be a compound of formula 17:

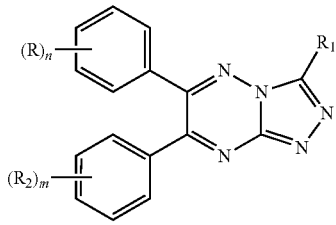

wherein, independently for each occurrence:

R and $R_2$ is hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ is H, hydroxy, amino, cyano, halide, alkoxy, ether, ester, amido, ketone, carboxylic acid, nitro, thiol, alkylthio, or a substituted or unsubstituted alkyl, aryl, aralkyl, heterocyclyl, heterocyclylalkyl, heteroaryl, or heteroaralkyl; and m and n are integers from 0 to 5 inclusive.

In a further embodiment, the antiviral compound is a compound of formula 17 and the attendant definitions wherein n is 0.

In a further embodiment, the antiviral compound is a compound of formula 17 and the attendant definitions wherein m is 0.

In a further embodiment, the antiviral compound is a compound of formula 17 and the attendant definitions wherein $R_1$ is SH.

In a further embodiment, the antiviral compound is a compound of formula 17 and the attendant definitions wherein n is 0 and m is 0.

In a further embodiment, the antiviral compound is a compound of formula 17 and the attendant definitions wherein n is 0, m is 0, and $R_1$ is SH.

An exemplary compound having formula 17 is compound 21 set forth in FIG. 1b.

Preferred compounds are compounds represented by formulas 2, 6, 9, 11, 15, and 17 as exemplified by compounds 5, 9, 12, 18, 20 and 21 in FIGS. 1a and 1b.

Also included herein are pharmaceutically acceptable addition salts and complexes of the compounds of formulas 1-17. In cases wherein the compounds may have one or more chiral centers, unless specified, each unique racemic compound, as well as each unique nonracemic compound is encompassed herein.

In cases in which the inhibitors have unsaturated carbon-carbon double bonds, both the cis (Z) and trans (E) isomers are provided herein. In cases wherein inhibitors may exist in tautomeric forms, such as keto-enol tautomers, such as

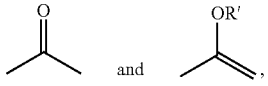

each tautomeric form is contemplated, whether existing in equilibrium or locked in one form by appropriate substitution with R'. The meaning of any substituent at any one occurrence is independent of its meaning, or any other substituent's meaning, at any other occurrence.

Also included herein are prodrugs of the compounds of formulas 1-17.

Compositions may also comprise at least 2, 3, 4, 5 or more compounds described herein. Compositions may also comprise at least one compound described herein and a second therapeutic compound, such as a second antiviral compound. For example, a composition may comprise at least one compound described herein and gancyclovir (ganciclovir), foscarnet, cidofovir and/or cytomegalovirus immunoglobulin.

Compositions, e.g., pharmaceutical compositions, comprising one or more compounds described herein may be present in vehicles for administration, e.g., stents and syringes. They may also be present in containers and in kits.

Results

Development of an assay to identify small molecule inhibitors of the UL54-UL44 interaction. To identify small molecule inhibitors of the UL54-UL44 interaction, we developed an assay based on fluorescence polarization (FP) (Dandliker et al., 1981). In this assay, a peptide corresponding to the C-terminal 22 residues of UL54 (here named peptide 1, as in Loregian et al. (Loregian et al., 2003)), which was labeled with the fluorophore Oregon Green, is mixed with UL44ΔC290, a truncated protein which retains all known biochemical activities of full-length UL44 (Loregian et al., 2004b), fused to glutathione S-transferase (GST-UL44ΔC290). Addition of increasing amounts of GST-UL44ΔC290 to a solution of 3 mM labeled peptide resulted in increasing FP (FIG. 4A). From the data in FIG. 4A, a $K_d$ value of ~1 μM was calculated for the interaction between GST-UL44ΔC290 and the UL54 peptide. This value is similar to that (0.52 μM) previously determined for GST-UL44ΔC290 and the corresponding unlabeled UL54 peptide using isothermal titration calorimetry (Loregian et al., 2004a). As a control, we also examined binding of a mutant GST-UL44ΔC290 (I135A), which is severely impaired for binding to both full-length UL54 and the UL54-derived peptide (Loregian et al., 2004b). Addition of GST-UL44ΔC290 I135A to labeled peptide 1 resulted in only a slight increase in FP at protein concentrations higher than 17.5 μM (FIG. 4A). Furthermore, no increase in FP was observed when the labeled peptide was incubated in the presence either of GST alone or of a fusion between maltose binding protein and the HSV-1 homolog of UL44, UL42 (MBP-UL42ΔC340). Thus, this assay could specifically and quantitatively measure interactions between UL44 and the UL54-derived peptide.

We next investigated whether this assay could detect a known inhibitor of the UL54-UL44 interaction. To this end, a binding reaction of 2.5 μM GST-UL44ΔC290 and 3 nM labeled peptide was titrated with increasing concentrations of unlabeled peptide 1 (FIG. 4B). This peptide has been shown to inhibit both the physical interaction between UL54 and UL44 and DNA synthesis by the UL54-UL44 complex (Loregian et al., 2003). We observed that FP from the UL44-peptide interaction was inhibited by unlabeled peptide 1 with a 50% inhibitory concentration ($IC_{50}$) of 5 μM. This value is of similar magnitude to that measured (11 μM) for inhibition of UL54-UL44 physical interaction by this peptide in an ELISA interaction assay (Loregian et al., 2003). A peptide corresponding to the last 36 residues of HSV-1 UL30 (peptide A), which has been shown to inhibit the interaction between HSV-1 UL30 and UL42 (Bridges et al., 2001; Bridges et al., 2000; Digard et al., 1995), did not cause decrease in FP (FIG. 4B). Thus, this assay could detect specific inhibition of the interaction between UL44 and the UL54-derived peptide.

High throughput screen. We then used the FP assay and the facilities of the Harvard Institute of Chemistry and Cell Biology (ICCB) to screen the Peakdale (2,816 compounds), Bionet (4,800 compounds), Maybridge (8,800 compounds), and ChemDiv (28,864 compounds) libraries, and 4,348 compounds out of the 50,000 of the Chembridge Microformat library. Thus, we screened a total of 49,628 compounds, each at a concentration of 12.5 μg/ml. As positive controls for inhibition, reaction mixtures of GST-UL44ΔC290 and labeled peptide in the presence of 3 μM or 20 μM of unlabeled peptide 1 were included on each screening plate. The criterion for an active compound was one that exhibited an FP value similar to or lower than that observed in binding reactions of GST-UL44ΔC290 and labeled peptide in the presence of 3 μM unlabeled peptide 1. 143 compounds (approximately 0.3% of the compounds screened) met this criterion. These compounds were then re-tested in the FP assay with GST-UL44ΔC290 and UL54-derived peptide. They were also assayed, at the same concentration used during the screen (12.5 μg/ml), in an FP assay that was used to discover inhibitors of interactions between HSV-1 DNA polymerase subunits (Pilger et al., 2004). This assay used MBP-UL42ΔC340 and a labeled HSV-1 UL30-derived peptide as previously described (Pilger et al., 2004). Of the 143 hits, only 25 (0.05% of the compounds screened) were found to specifically inhibit the UL54 peptide-UL44 but not the UL30-UL42 interaction in FP assays. Of the other 118 compounds, 97 inhibited the UL30-UL42 interaction, and 21 were not active in both assays. Among the 25 specifically active compounds, 21 small molecules, which were designated AL1 to AL21 (FIGS. 1a and 1b), were commercially available and were purchased for further studies. Among these compounds, two classes with similar structure are recognizable, a class composed by AL1, AL2, AL3, and AL4, and another class composed by AL8 and AL21. The remaining compounds are not obviously similar. None of these molecules was identical to any compound previously identified in screening at the ICCB for inhibition of different protein-protein interactions.

Dose dependence of inhibition. Next, we performed dose-response analyses of the inhibition of the UL44-UL54 peptide interaction for each of the 21 compounds in FIGS. 1a and 1b. Of these, nine compounds—AL5, AL6, AL8, AL9, AL10, AL11, AL12, AL18, and AL21—reproducibly exhibited a dose-dependent reduction in FP with $IC_{50}$ values lower than 50 μM (values ranged from 5 to 30 μM; see FIG. 5A and Table 2). Two other compounds, AL13 and AL15, inhibited FP in dose-dependent manner, but with higher $IC_{50}$ values (50 and 60 μM, respectively; Table 2). The remaining 10 compounds did not reproducibly inhibit UL44-UL54 peptide binding in FP assays in a dose-dependent manner (FIG. 5 and Table 2). As a control, varying concentrations of the active compounds were also tested in the FP assay for inhibition of the HSV-1 DNA polymerase subunit interaction (Pilger et al., 2004). None of the compounds exhibited a dose-dependent reduction in FP in these assays (FIG. 5B and data not shown).

Specific inhibition of long-chain DNA synthesis mediated by UL44. To analyze the ability of the compounds to interfere with functional UL54-UL44 interactions, we tested their ability to inhibit long-chain DNA synthesis by UL54 in the presence of UL44 employing a poly(dA)-oligo(dT)$_{12-18}$ template-primer. In this assay, no long-chain DNA synthesis was detected in the presence of UL54 alone (FIG. 7A, lane 1), or of GST-UL44ΔC290 alone (lane 3), while formation of long DNA products was observed when both UL54 and GST-UL44ΔC290 were present (lane 2). An equal concentration (40 μM) of each of the 21 compounds in FIGS. 1a and 1b was initially tested for inhibition of long-chain DNA synthesis by UL54 and UL44. Five compounds (AL5, AL9, AL12, AL18, and AL21) severely decreased formation of long DNA products, while the remaining compounds did not measurably affect long-chain DNA synthesis (data not shown).

To test the dose-dependence of inhibition and quantify the effects on long-chain DNA synthesis, different doses of the active compounds (AL5, AL9, AL12, AL18, and AL21) and of four other hits from the screen (AL1, AL2, AL3, and AL20) were tested. As a control for inhibition, various concentrations of peptide 1, which was previously shown to inhibit the rate of incorporation of nucleotides with an $IC_{50}$ of 20 μM (Loregian et al., 2003), were also assayed. These data were quantified by phosphorimager analysis, and the $IC_{50}$ values for inhibition of long-chain DNA synthesis were calculated (FIG. 7B and Table 2). Peptide 1 inhibited long-chain DNA synthesis with an $IC_{50}$ of 18 μM (FIG. 7A, lane 4 to 8, and FIG. 7B). AL5, AL9, AL12, AL18, and AL21 inhibited formation of long DNA products in a dose-dependent manner with $IC_{50}$ values ranging from 5 μM to 15 μM (FIGS. 7A and 7B). In contrast, AL1, AL2, AL3, and AL20 exhibited little or no inhibition of long-chain DNA synthesis by UL54 and UL44 (FIGS. 7A and 7B and Table 2).

Figure 8:
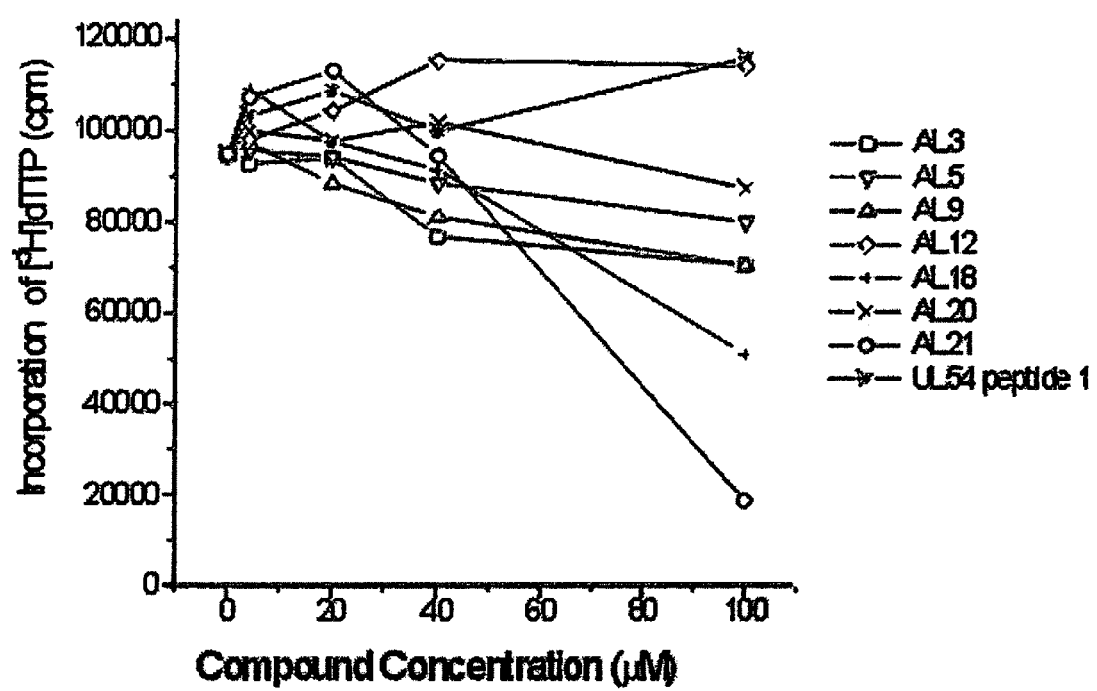
FIG. 8 depicts the effect of selected compounds on the physical interaction of UL44 with full-length UL54. The interaction between purified baculovirus-expressed UL54 and UL44 proteins was measured using an interaction ELISA assay in the presence of varying concentrations of AL3, AL5, AL9, AL12, AL18, AL20, and AL21, and of peptide 1 as a positive control.

To determine whether the inhibition of long-chain DNA synthesis could be due to effects on the catalytic activity of the UL54 subunit, rather than on effects on UL44-mediated DNA synthesis, we tested varying concentrations of each of the 21 compounds in FIGS. 1a and 1b for their effects on DNA synthesis by UL54 alone using a filter-binding assay previously described (Loregian et al., 2003). As summarized in Table 2, only compounds AL2 and AL21 inhibited the activity of UL54 alone, but only at high concentrations ($IC_{50}$'s of 95 and 78 μM, respectively). However, AL21 inhibited the activity of UL54 alone much less potently than the activity of the UL54-UL44 combination (compare FIG. 7B and FIG. 8), suggesting a specific effect on UL44-mediated long-chain DNA synthesis. All other compounds exhibited little or no inhibition of UL54 catalytic activity ($IC_{50}$ values>100 μM; see FIG. 8 and Table 2).

Figure 6:
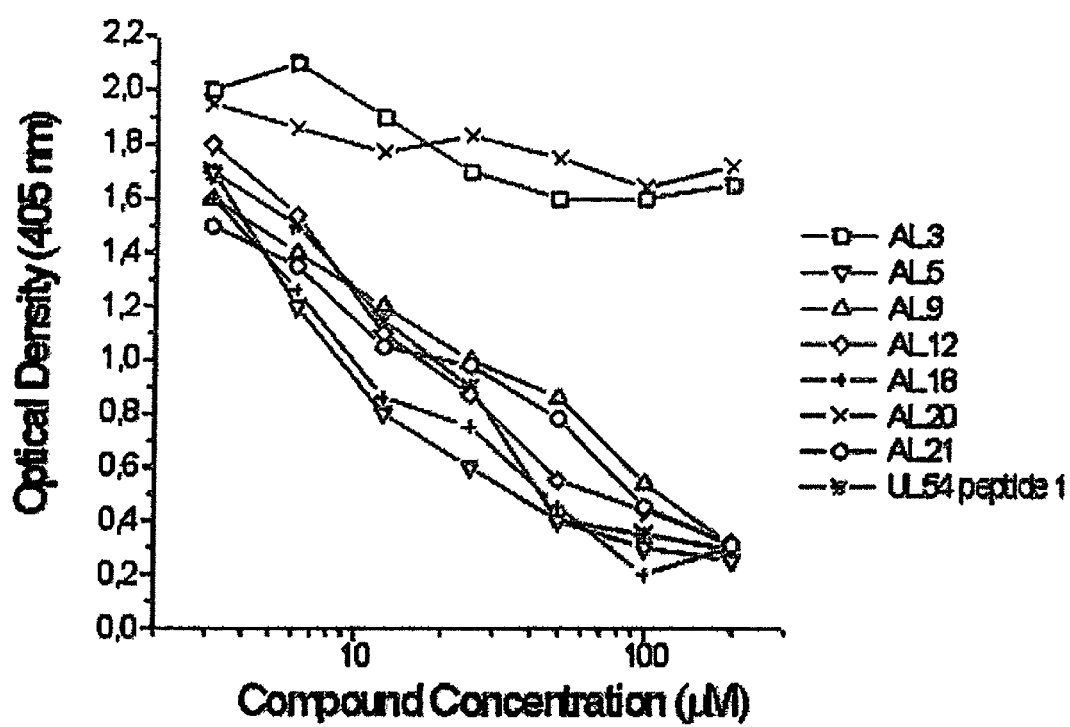
FIG. 6 depicts the effect of selected compounds on DNA synthesis activity by UL54 alone. The DNA polymerase activity of in vitro expressed UL54 protein was measured in the presence of varying concentrations of compound AL3, AL5, AL9, AL12, AL18, AL20, and AL21, and peptide 1, by incorporation of [$^3$H]dTTP into a poly(dA)-oligo(dT) DNA template. Samples were taken after 20 min of incubation at 37° C. and spotted onto DE81 filters. The filters were washed and radioactivity was counted.

Specific inhibition of the physical interaction of UL44 with full-length UL54. We next wished to determine if the compounds that inhibited the UL44-UL54 functional interaction could inhibit the physical interaction of UL44 with full-length UL54 using an ELISA interaction assay. In this assay, binding between purified baculovirus-expressed UL54 and UL44, which was tagged with an EEF epitope, was detected using an antibody that recognizes the epitope tag (Loregian et al., 2003). This assay was used to test the five compounds that had specifically inhibited long-chain DNA synthesis by UL54-UL44 (AL5, AL9, AL12, AL18, and AL21), two other compounds that had scored as hits in the initial assay (AL3 and AL20), and peptide 1 as a control. Peptide 1 exhibited an $IC_{50}$ for inhibition of the UL54-UL44 interaction of 15 μM, a value similar to that (11 μM) previously determined using the same assay (Loregian et al., 2003). Consistent with the results of the long chain DNA synthesis assay, compounds AL5, AL9, AL12, AL18, and AL21 were able to interfere with the physical interaction between UL44 and full-length UL54, with $IC_{50}$ values ranging from 7 to 19 μM, whereas compounds AL3 and AL20 did not significantly inhibit the UL54-UL44 interaction at concentrations up to 200 μM (FIG. 6).

Antiviral and cytotoxic activity. We then investigated the antiviral effects of the 21 compounds in human foreskin fibroblast (HFF) cells. First, we tested all 21 compounds in plaque reduction assays, which entail viral infection at low multiplicity. GCV was included in these experiments as a control for inhibition. GCV exhibited an $ED_{50}$ of 1.9 μM, a value in the range of those previously reported (0.43 to 7 μM; (Faulds and Heel, 1990)). AL5, AL9, AL12, AL18, and AL21, the compounds that inhibited both physical and functional interactions between UL54 and UL44 in biochemical assays, also inhibited plaque formation by HCMV AD169 with 50% effective dose ($ED_{50}$) values from 1.1 to 10 μM (FIG. 9A and Table 2). Although not active in biochemical assays, other compounds, namely AL14, AL16, AL19, and AL20, exhibited activity against virus plaque formation ($ED_{50}$ values <30 μM; FIG. 9A and Table 2).

Next, we tested the effects of selected compounds and of GCV as a control in viral yield assays, which measure the titer of virus progeny produced following infection at relatively high multiplicity. In these assays, the viral titer was measured at two different times points post-infection (p.i.): at 96 hrs, when the release of virus progeny is increasing, and at 120 hrs, when the titer of virus progeny after a single cycle of replication reaches peak levels (Stinski, 1983). Virus titers from untreated infected cells were $1.25 \times 10^5$ PFU (plaque forming unit)/ml and $3.87 \times 10^6$ PFU/ml at 96 hrs and 120 hrs p.i., respectively. Compounds AL5, AL9, AL12, AL18, and AL21, which were active in the biochemical assays for inhibition of UL54-UL44 interactions, inhibited virus yield with $ED_{50}$ values at 96 hrs p.i. ranging from 0.3 to 8 μM (Table 2) and with $ED_{50}$ values at 120 hrs p.i. ranging from 0.4 to 4 μM (FIG. 9B and Table 2). GCV exhibited an $ED_{50}$ of 0.9 µM at 96 hrs p.i. and of 0.8 µM at 120 hrs p.i. in these assays. Of the compounds that were inactive for inhibition in biochemical assays for inhibition of UL54-UL44 interactions, compound AL20 showed significant antiviral activity ($ED_{50}$=4.0 µM at 120 hrs p.i.), whereas compounds AL1, AL2, AL3, and AL4 exhibited little or no effect on HCMV replication (FIG. 9B and Table 2).

Figure 10:
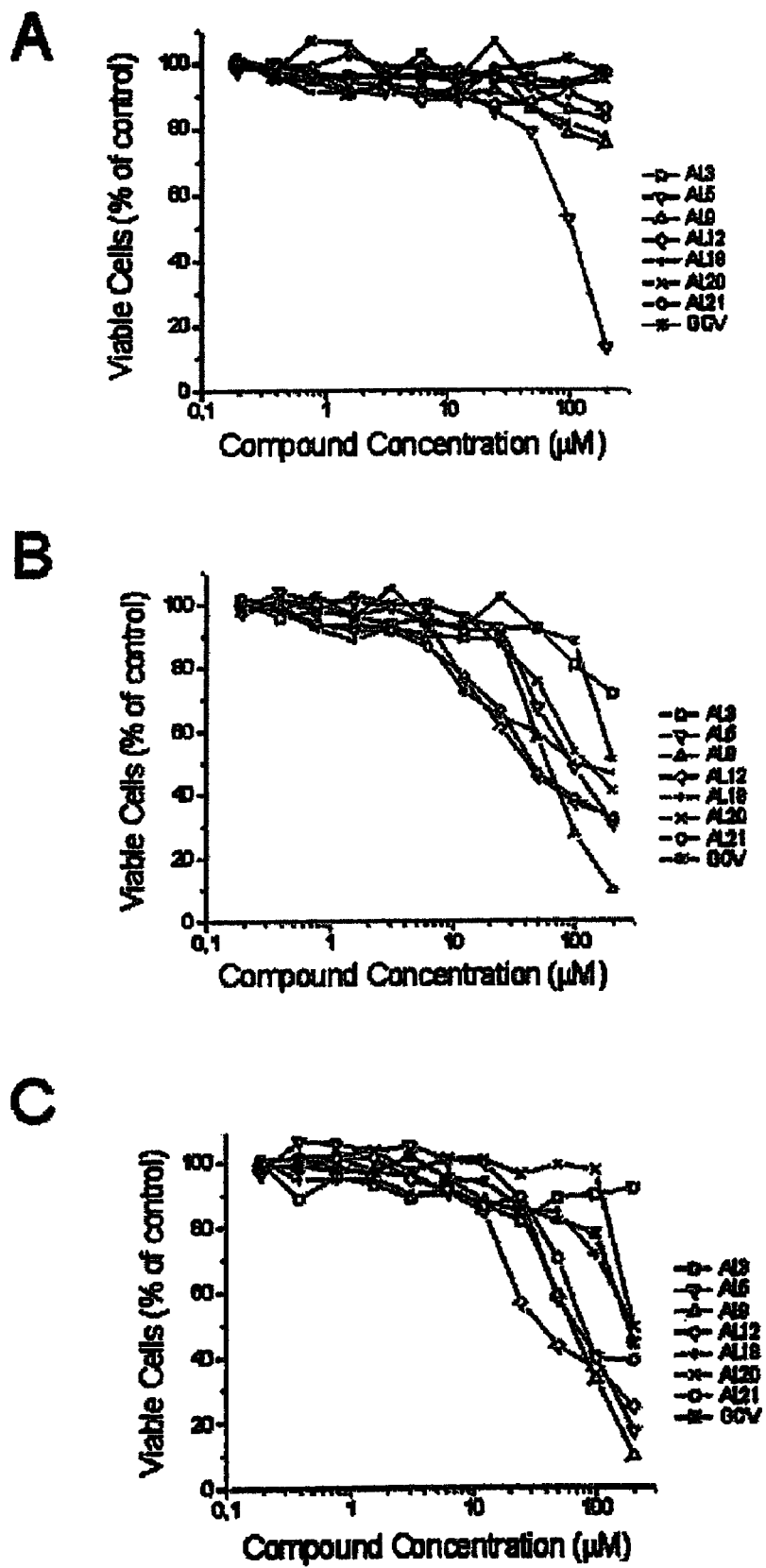
FIG. 10 depicts cytotoxicity of selected compounds. The effect of AL3, AL5, AL9, AL12, AL18, AL20, AL21, and GCV on HFF cell viability were measured using an XTT assay at 24 hrs (A), 72 hrs (B), or 120 hrs (C) following the addition of compound to cell media. The absorbances measured in the XTT assay were plotted onto a standard curve of number of cells versus absorbance to calculate the percentage of viable cells remaining.
Figure 11:
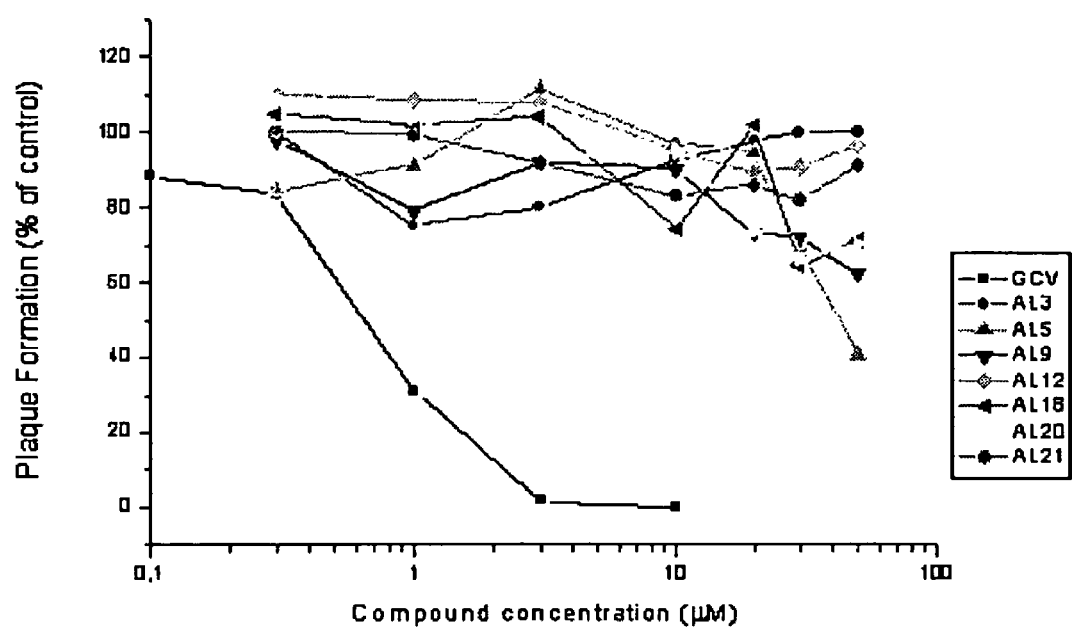
FIG. 11 depicts a plaque reduction assay to test activity of GCV and A1 compounds against HSV-1.
Figure 12:
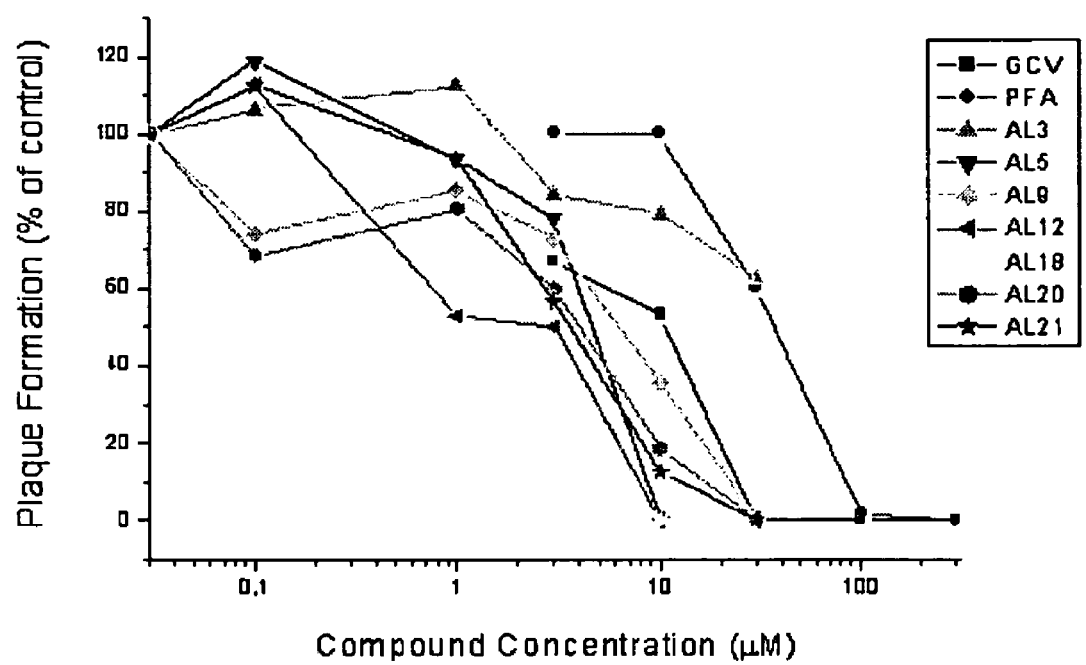
FIG. 12 depicts a summary of activities of AL compounds against a GCV-resistant HCMV strain (759rD100).
Figure 13:
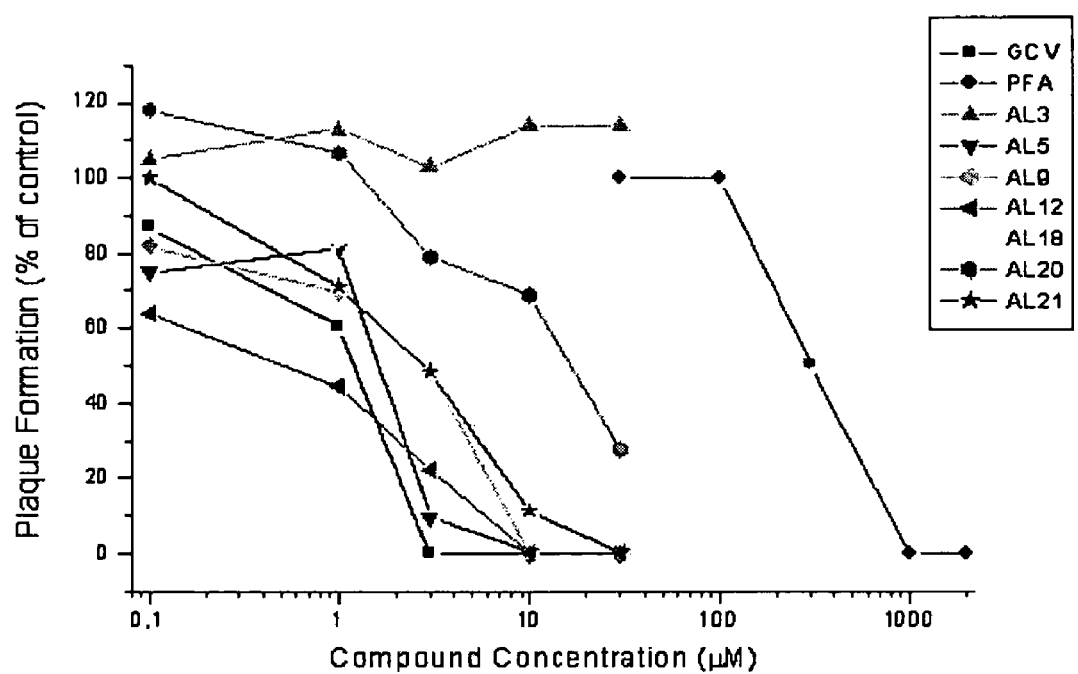
FIG. 13 depicts a summary of activities of AL compounds against a PFA-resistant HCMV strain (PFArD100).

In parallel, we tested the cytotoxicity of all 21 compounds and of GCV in HFF cells using a dye-uptake (XTT) assay. GCV showed a $CC_{50}$ (concentration that cause a decrease of cell viability of 50%) around 200 µM (FIG. 10 and Table 2), a value that is the range of those previously reported (40-800 µM; (Faulds and Heel, 1990)). Compounds AL6, AL10, AL11, AL13, AL14, AL16, and AL19 exhibited significant cytotoxicity in this assay. Importantly, for compounds AL10, AL13, AL14, AL16, and AL19, the $CC_{50}$ values were similar to the $ED_{50}$'s measured in antiviral assays (Table 2). Thus, the effects of these compounds observed in antiviral assays are likely due to cytotoxicity rather than to specific antiviral activity. In contrast, compounds AL5, AL9, AL12, AL18, AL20, and AL21 showed cytotoxicity at concentrations from 7- to 500-fold higher than those at which they exhibited antiviral activity (FIG. 10 and Table 2). Thus, these small molecules appear to exhibit selective anti-HCMV activity. Among these six compounds, five—i.e., AL5, AL9, AL12, AL18, and AL21—also specifically inhibited physical and functional interactions between UL54 and UL4. One compound, AL20, although originally identified in our high throughput screen, was not active in biochemical assays of UL54-UL44 interactions. Thus, the mechanism of this compound is likely to be different.

Discussion

In this study, we identified five small molecules with diverse structures that selectively inhibit the physical interaction between the subunits of HCMV DNA polymerase and its functional consequences. These compounds did not detectably inhibit the interaction between the accessory subunit and the C-terminus of the catalytic subunit of HSV-1 DNA polymerase. Nor did they inhibit basal DNA polymerase activity of the HCMV catalytic subunit alone, except in one case at high concentrations. These five compounds also exhibited anti-HCMV activity with sub- to micromolar potencies. Importantly, these compounds exhibited much less potent cytotoxic activities than antiviral activities.

Small molecules that selectively inhibit HCMV polymerase subunit interactions. As protein-protein interfaces are crucial to most biological processes and often determine specificity, they can, in principle, be excellent targets for drug discovery. However, while there are numerous reports in the literature of the use of dominant negative proteins, antibodies, or peptides to inhibit protein-protein interactions, there are only a few examples of small "drug-like" molecules that selectively disrupt these interactions. Several factors seem likely to have contributed to our ability to add AL5, 9, 12, 18, and 21 to that number. Although the UL54-UL44 interaction involves a number of contacts between UL54 and UL44 (Appleton et al., submitted), only a few of these are crucial. In particular, when either Leu1227 or Phe1231 of UL54 is substituted with alanine, no detectable interaction between UL54 and UL44 is observed (Loregian et al., 2004a). These two residues help form a hydrophobic "plug" that packs against a hydrophobic crevice on UL44 (Appleton et al., submitted). It is easy to envision a small molecule being able to specifically disrupt this interaction. Along these lines, it is interesting to note that of two related compounds that were active in the FP assay, AL21 was active against long chain synthesis by HCMV DNA polymerase, while the larger AL8 was inactive. We speculate that the larger AL8 makes non-productive interactions with full-length UL54 that AL21 does not.

It is interesting to compare the compounds identified in this study and BP5, a small molecule that specifically inhibits the physical and functional interactions between the two subunits of HSV-1 DNA polymerase, UL30 and UL42 (Pilger et al., 2004). BP5 has more peptide-like qualities than does AL5, AL9, AL12, AL18, or AL21, which include more aromatic properties. This difference may relate to the major difference between the HSV-1 UL30-UL42 interaction, which relies on critical hydrogen-bonding interactions (Bridges et al., 2001; Zuccola et al., 2000), and the HCMV UL54-UL44 interaction, which involves hydrophobic interactions (Loregian et al., 2004a; Loregian et al., 2004b); Appleton et al., submitted.), even though these interactions both involve the C-terminus of each catalytic subunit and the connector loop of the other subunit. It is therefore not surprising that BP5 does not inhibit the HCMV UL54-UL44 interaction (Pilger et al., 2004), while none of the compounds studied here inhibited the HSV-1 UL30 peptide-UL42 interaction (FIG. 5B and data not shown). These differences emphasize that highly specific nature of these polymerase subunit interactions, which also share no sequence homology.

Selective inhibitors of HCMV replication. Because HCMV is such a serious pathogen in newborns and in immunocompromised individuals, and because current drugs have important toxicities and/or pharmacokinetic drawbacks, we were especially heartened to observe relatively potent inhibition of HCMV replication. The potencies observed were similar to those of ganciclovir, the drug of choice for the treatment of most HCMV infections (Markham and Faulds, 1994). They are comparable to published values for cidofovir, for which $IC_{50}$ values from 0.5 to 2.8 µM have been described (Snoeck et al., 1988) and significantly greater than that of foscarnet, for which $IC_{50}$ values from 23 to 81 µM have been reported (Markham and Faulds, 1994), and comparable to that of cidofovir. At least as important, these small molecules, without any modifications, exhibit relatively cytotoxic activities similar to those of the current anti-HCMV drug of choice, ganciclovir, and only slightly greater than those reported for foscarnet and cidofovir (600 µM, and 360 µM, respectively; Faulds and Heel, 1990; Snoeck et al., 1988). Crystal structures of UL44, either unliganded or bound to the C-terminus of UL54 have been solved (Appleton et al., 2004; Appleton et al. submitted). This makes feasible studying how the compounds bind to their target in molecular detail and using that information to guide modifications of the compounds in order to increase their antiviral activity and decrease their cytotoxicity.

It is worth notable that all five of the compounds that inhibited long chain DNA synthesis by the UL54/UL44 combination exhibited antiviral activity, while fifteen out of the sixteen compounds that failed to inhibit long chain DNA synthesis also failed to inhibit HCMV replication. This strong correlation suggests that the anti-HCMV activity of our compounds is due to inhibition of viral polymerase subunit interactions inside infected cells. However, further study is needed to determine if this is indeed the antiviral mechanism.

The inhibitors of HCMV DNA polymerase subunit interactions that we have identified may have some theoretical advantages when compared with other classes of anti-HCMV compounds. First, following phosphorylation, drugs such as GCV and cidofovir mimic natural nucleotide substrates of host enzymes, which can lead to toxicities such as mutagenesis, as documented for GCV (Morris, 1994). The new, nonnucleoside compounds identified here would not be expected to exhibit similar toxicities, although other kinds of toxicities cannot be excluded. Second, GCV, cidofovir, and foscarnet act via inhibition at sites in HCMV DNA polymerase that are conserved among human and viral enzymes. Indeed, mutations that confer resistance to these compounds usually alter such conserved residues. In contrast, compounds that inhibit protein-protein interactions are expected to be highly specific, as protein-protein interactions themselves are highly specific. In the case of herpesvirus DNA polymerase subunit interactions, although the most important residues lie in analogous regions, i.e. the C-terminus of the catalytic subunit and the so-called connector loop of the accessory protein, the sequences of these segments differ considerably. Moreover, the side chains of the residues that have been identified as important for HSV-1 UL30-UL42 and for HCMV UL54-UL44 interaction are different, being hydrophilic in the first case (Bridges et al., 2001) and hydrophobic in the latter (Loregian et al., 2004a; Loregian et al., 2004b). The differences between HCMV and HSV DNA polymerase subunit interactions herald the prospect that small molecule inhibitors targeting such interactions could be significantly more specific than most of the drugs currently licensed for anti-herpesvirus chemotherapy. In support of this hypothesis, the small molecules able to block the UL54-UL44 interaction did not detectably inhibit the binding between the subunits of HSV-1 polymerase (FIG. 5). Furthermore, the details of the UL54-UL44 interaction differ substantially from those of the human processivity factor, PCNA, and its binding partners (Appleton et al.,) Third, our new compounds, which target sites on the viral polymerase different from those targeted by GCV, cidofovir, and foscarent, should be active against viruses resistant to these drugs. An interesting question is whether compounds that target protein-protein interactions might be less prone to drug resistance than are inhibitors that bind enzyme active sites.

Thus, the small molecules that we have identified will be useful as antiviral compounds and also represent an interesting starting point for the discovery of new, non-substrate-based drugs that may be more potent and specific than currently existing anti-HCMV agents and that should be active against viral mutants resistant to these compounds.

Significance. HCMV is an important pathogen in the immunocompromised, including transplant recipients and patients with AIDS, and in newborns where it is a leading infectious cause of birth defects (Pass, 2001). Although there are several antiviral drugs licensed for the treatment and prophylaxis of HCMV infections, these all suffer from problems with toxicity, drug resistance, and/or pharmacokinetic drawbacks. Most of these drugs, including the front-line therapy, ganciclovir, work via inhibition of the viral DNA polymerase by binding to active sites that contain residues conserved among human and viral enzymes. In contrast, the residues that comprise the interaction interface between UL54 and UL44 are not conserved with their human counterparts or even with counterparts from other herpesviruses. Thus, a small molecule that specifically inhibits this interaction should avoid the kinds of toxicities observed with current anti-HCMV polymerase inhibitors. It is therefore encouraging that the molecules that we have identified selectively inhibit HCMV polymerase subunit interactions and exhibit sub- to low micromolar potency against HCMV. Even more encouraging are the relatively low potencies of these compounds in assays of cytotoxicity. Indeed, even without the benefit of any medicinal chemistry to modify these compounds, their cell-based therapeutic indices are similar to that of ganciclovir. As these compounds are diverse in structure and the crystal structure of UL44 both unliganded and bound to the C-terminus of UL54 have been solved, prospects for modifying at least one of these into a safer, more potent anti-HCMV drug seem promising.

Exemplary Methods

The compounds described herein can be used for treating or preventing a viral infection, such as a herpes infection, and in particular, an infection by HCMV. Other viruses against which the compounds described herein may be effective include those having a similar catalytic subunit to UL54 of a polymerase and a similar accessory protein UL44. Exemplary viruses include β-herpesviruses, such as human herpesvirus 6 and human herpesvirus 7 (HHV-6 and HHV-7, respectively).

In an illustrative embodiment, a therapeutically effective amount of a compound having a formula selected from formulas 1-17, or a pharmaceutically acceptable salt, prodrug or ester thereof, is administered to a subject, such as a subject in need thereof. A subject may be a mammal, such as a human or a non-human animal, e.g., a canine, feline, equine, bovine, ovine, porcine or sheep.

The present invention further provides the use of the compounds described herein for the treatment and/or prophylaxis of diseases, especially of infections with viruses, in particular the viruses mentioned herein, and the infective diseases caused by these infections. The present invention also provides the use of the compounds described herein for the treatment and/or prophylaxis of disorders, in particular the disorders mentioned herein. The present invention also provides the use of the compounds described herein for preparing a medicament for the treatment and/or prophylaxis of disorders, in particular the disorders mentioned herein. The compounds described herein are preferably used for preparing medicaments suitable for the prophylaxis and/or treatment of infections with a representative of the group of the Herpes viridae, in particular a cytomegalovirus, in particular the human cytomegalovirus. The present invention also provides a method for the treatment and/or prophylaxis of disorders, in particular the disorders mentioned herein, using an antivirally effective amount of the compounds described herein.

Areas of indication which may be mentioned by way of example are:
1) Treatment and prophylaxis of HCMV infections in AIDS patients (retinitis, pneumonitis, gastrointestinal infections).
2) Treatment and prophylaxis of cytomegalovirus infections in bone-marrow and organ transplantations which develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.
5) Treatment of HCMV infection in immunosuppressed patients associated with cancer and cancer therapy.
6) Treatment of HCMV-positive cancer patients with the aim to reduce HCMV-mediated tumour progression (cf. J. Cinatl, et al., FEMS Microbiology Reviews 2004, 28, 59-77).

A subject who may benefit from a treatment described herein may be an infant at risk of or having a congenital infection or a pregnant woman who is infected with HCMV during the pregnancy. A subject may also be a subject who has or may develop a life-threatening disease following either a primary infection with HCMV or reactivation. Common syndromes include interstitial pneumonia, retinitis, enteritis, or disseminated infection.

The compound may be in a pharmaceutical composition, e.g., comprising a pharmaceutically acceptable vehicle. As further described below, a pharmaceutical composition may be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An antiviral treatment may comprise the administration of one or more compounds described herein. A treatment may comprise a single administration of a compound, or two or more administrations. In certain situations, a treatment may comprise a daily administration of a compound for several days, one week, several weeks, one month or several months. Exemplary dosages are further described herein.

A treatment may comprise administration of a compound described herein as well as a second therapeutic compound, e.g., an antiviral compound, such as gancyclovir (ganciclovir), foscarnet, cidofovir and/or cytomegalovirus immunoglobulin. These may be administered simultaneously or sequentially.

In certain embodiments, a subject is first diagnosed with a viral infection, such as an HCMV infection, according to methods known in the art, and then treated as described herein. In other embodiments, a subject is treated preventatively. For example, a subject at risk of being infected with a virus, e.g., HCMV, is treated as described herein. A subject at risk of being infected may be a subject who is in close contact with infected subjects or a subject who is immunodeficient, such as a subject infected with HIV.

The presence of HCMV may be diagnosed by the detection of the virus or antibodies thereto (IgG and/or IgM) in a bodily fluid. HCMV can be found in, e.g., blood, urine, saliva, respiratory secretions, tears, feces, breast milk, semen and cervical secretions. Hematologic tests will show a relative lymphocytosis with more than 50% of the peripheral white blood cell count composed of lymphocytes. From these 10% or more are atypical lymphocytes. Other diagnostic tests include examination of urine for cells with intranuclear inclusions, which test is useful, e.g., in newborns. Various serologic methods that can be used include fluorescence assays, indirect hemagglutination, latex agglutination and enzyme immunoassays. Another test includes determining the presence of HCMV antigen in a patient's white blood cells, e.g., by immunofluorescence.

A therapeutic or prophylactic treatment may mirror a regimen using another antiviral drug, such as gancyclovir. Thus, a therapeutic treatment of a subject with a compound described herein, such as AL5, 9, 12, 18, 20 and 21, or an analog thereof, may comprise the intravenous administration of about 10 mg/kg/d in two divided doses for about 14 to 21 days. For long term suppression, administration may be at about 5 mg/kg/d for about 5 to 7 d/week. For prophylaxis of CMV, treatment may include administration of a compound at about 10 mg/kg/d in two doses for about 1 week, then about 5 mg/kg/d in one dose for about 100 days.

After one or more administrations of a composition described herein, a subject may be tested for the presence and/or level of the virus, e.g., to determine the effectiveness of the treatment on the subject.

A compound may be in a sterile solution, such as a sterile injectable composition, e.g., a sterile injectable aqueous or oleaginous suspension, which can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

The carrier in a pharmaceutical composition is preferably "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the indole compounds, or one or more solubilizing agents, can be utilized as pharmaceutical excipients for delivery of the purine compounds. Examples of other carriers include colloidal silicon dioxide, magnesium stearate, cellulose, sodium lauryl sulfate, and D&C Yellow #10.

Pharmaceutical compositions may be administered intravenously. Such compositions are advantageously administered "piggyback" with generally accepted intravenous fluids. An induction treatment may include from about 2 milligrams/kg/day to about 10 milligrams/kg/day of the active ingredient (administered over a constant rate for one hour twice a day) for 2 to 3 weeks.

A maintenance treatment may include from about 1 milligram/kg/day to about 5 milligrams/kg/day of the active ingredient (administered over a constant rate for one hour once a day), increasing to double the dosage if symptoms reoccur. Of course, it will be appreciated that there are many factors which affect the actual dosage needed under the circumstances such as the state of the disease, the pharmacological activity of the active ingredient, and the patient's individual susceptibility to the active ingredient.

As used herein, a pharmaceutical composition may include emodin, emodin anthrone, emodin bianthrones, protohypericin, hypericin, rhein, alizarin, quinalizarin, quinizarin, and 1,8-dihydroxyanthraquinone, related hydroxyanthraquinones, hydroxyanthrones, or dimers thereof, or mixtures thereof including salts and other pharmacologically active forms thereof, which have been shown to possess anti-HCMV activity.

The pharmaceutical compositions may also be administered systemically in oral solid dosage forms, ophthalmic, suppository, aerosol, or other similar dosage forms. In addition to the active ingredient, such pharmaceutical compositions may contain pharmaceutically acceptable carriers and other ingredients known to enhance and facilitate drug administration.

For example, a composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. The active ingredient may also be incorporated into a liquid or syrup form in an alcohol or glycerin base. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

The initial oral dosage of active antiviral compounds may be in the range from about 10 mg/kg/day to about 100 mg/kg/day, e.g., in three divided doses for approximately 10 days. Thereafter, a maintenance dosage of from about 1 mg/kg/day to about 50 mg/kg/day in three divided doses may be administered to the patient.

Tablet or capsules may be formulated with suitable binders and pharmacologically acceptable carriers such as starch, gelatin, sugars, natural and synthetic gums, carboxymethylcellulose, polyvinylpyrrolidone, Veegum, waxes, and ethyl cellulose; disintegrants such as starches, clays, celluloses, algins, gums, cross-linked polymers, and bentonite; lubricants such as talc, magnesium stearate, calcium stearate, and stearic acid; diluents such as microcrystalline cellulose (Avicel); and colorants such as United States approved FD&C dyes.

Typical tablets may be film coated, sugar coated, microencapsulated or impression coated and may possibly be controlled release or enteric coated. Tablets or capsules containing active antiviral compounds may be administered orally, sublingually, or transmucosally in the vagina or buccal pouch.

The following is a typical tablet formulation prepared by the wet granulation method:

| Ingredients | Per Tablet |
| --- | --- |
| Active antiviral compound | 0.3 to 33 mg |
| Polyvinylpyrrolidone | 22.5 mg |
| Lactose | 61.8 mg |
| Alcohol 3A-200 proof | 4.5 ml |
| Stearic acid | 9 mg |
| Talc | 13.5 mg |
| Corn starch | 43.2 mg |

See Remington's Pharmaceutical Sciences, A. R. Gennaro, ed., Mack Publishing Co., Easton, Pa., p. 1621 (1985).

The following is a typical tablet formulation prepared by the direct compression method:

| Ingredients | Per Tablet |
| --- | --- |
| Active antiviral compound | 0.3 to 33 mg |
| Microcrystalline cellulose | 159 mg |
| Stearic acid | 9 mg |
| Colloidal silica | 2 mg |

See Remington's Pharmaceutical Sciences, p. 1622.

Pharmaceutical compositions comprising compounds described herein may also be advantageously formed into suppositories for rectal and vaginal administration. Rectal compositions may include from about 1 mg to about 50 mg of active antiviral compound in a 2 gram dose. In addition to the active ingredient, rectal compositions may include a suppository base such as natural or synthetic triglycerides, gelatins, and other known suppository bases known in the art.

A typical rectal suppository might include from about 0.1% to about 5% of the active antiviral compound in a base of approximately 75% polyethylene glycol of 1,000 molecular weight and 25% polyethylene glycol of 4,000 molecular weight. This suppository base has shown good heat stability. Another possible suppository base may be prepared from approximately 96% polyethylene glycol of 1,000 molecular weight and 4% polyethylene glycol of 4,000 molecular weight.

Other suppository bases known in the art, such as cocoa butter, glycerinated gelatin, hydrogenated vegetable oils, mixtures of polyethylene glycols of various molecular weights, and fatty acids esters of polyethylene glycol may also be used.

Vaginal compositions may include from about 50 mg to about 250 mg of active antiviral compound in a 5 gram dose. In addition to the active ingredient, vaginal compositions may include a suppository base such as those known in the art. A typical vaginal suppository might include from about 1% to about 5% of the active antiviral compound in a glycerinated gelatin base with 0.025% methylparaben and 0.015% propylparaben as preservatives. Other preservatives known in the art may also be used.

Pharmaceutical compositions may comprise ophthalmic dosage forms such as ointments or suspensions. A typical ophthalmic ointment may include from about 3% to about 5% active antiviral compound in a petrolatum base. Petrolatum bases known in the art may be used such as a 60:40 mixture of solid and liquid petrolatum. A petrolatum base allows for longer drug contact time and generally greater drug bioavailability. The petrolatum base is also nonirritating to the eye and provides good stability and storage. Mineral oil with petrolatum, anhydrous lanolin, or a polyethylene/mineral oil gel are possible substitutes for the petrolatum base.

A preservative, such as 0.004% benzalkonium chloride may be included in the ophthalmic ointment. Other possible ophthalmic preservatives which may be used include chlorobutanol, parahydroxy benzoates, aromatic alcohols, organic mercurials, and quaternary ammonium compounds.

A typical ophthalmic suspension may include from about 1% to about 3% active antiviral compound in an aqueous solution. Suitable aqueous solutions used in the art as ophthalmic suspensions may be used. One typical solution includes the antiviral compound in sodium phosphate (a buffer), sodium chloride, and 0.002% thimerosal as a preservative. The buffer maintains the pH of the suspension within the range from about 7.2 to about 7.6, and optimally at a pH of about 7.4 which is the pH of the tear fluid.

Drops of either an ophthalmic ointment or suspension may be used every two hours. Ophthalmic ointments are particularly useful in treating retinitis. However, in more progressive stages of the disease both ophthalmic ointment and oral dosage forms would likely be used.

A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A purine compound-containing composition can also be administered in the form of suppositories for rectal administration.

Compounds may also be administered in the form of an aerosol. For such administration of the pharmaceutical compositions, from about 50 mg to about 200 mg of the active antiviral compound may be administered per delivery. Suitable aerosol dosage forms include both solutions and suspensions. Aerosol dosage forms may be used to provide local activity in the nasal areas, throat, and lungs, such as in the treatment of pneumonitis. Rapid systemic activity may be obtained when the aerosol dosage form is absorbed from the lungs directly into the bloodstream, thereby bypassing the digestive system.

An aerosol solution may include the following ingredients: (1) Active antiviral compound, solubilized in ethanol with or without a surfactant (such as Tween); (2) Preservatives, such as cetylpyridinium chloride; (3) Antioxidants, such as ascorbic acid; (4) Solvent blend, such as water, ethanol, glycols; and (5) Propellants, such as $CCl_2F_2/CCl_{23}F$, $CCl_2F_2/C_2Cl_2F_4$, or $CCl_2F_2$ alone.

An aerosol suspension may include the following ingredients: (1) Active antiviral compound, micronized and suspended; (2) Dispersing agents, such as sorbitan oleate, oleyl alcohol, etc.; (3) Density modifiers; (4) Bulking agents; and (5) Propellants, such as $CCl_2F_2/CCl_{23}F$, $CCl_2F_2$/C2 $Cl_2F_4$, or $CCl_2F_2$ alone.

Aerosolization for both solutions and suspensions may be achieved using a variety of self-pressurized packages.

Other possible dosage forms, such as nanoparticles, liposomes, resealed erythrocytes, and immunologically based systems may also be used to administer active ingredients.

Nanoparticles are one of several types of systems known collectively as colloidal drug delivery systems. Microcapsules, nanocapsules, macromolecular complexes, polymeric beads, microspheres, and liposomes are considered nanoparticles. A nanoparticle is a particle containing a dispersed drug with a diameter of 200-500 nm. The size of the nanoparticle allows it to be administered intravenously via injection.

When phospholipids are dispersed in aqueous media, multilamellar concentric bilayer vesicles may be formed with aqueous media separating the lipid bilayers. These systems are commonly referred to as multilamellar liposomes or vesicles and have diameters from 25 nm to 4 μm. Sonication of multilamellar liposomes results in the formation of small unilamellar vesicles with diameters in the range of 200-500 Å, containing aqueous solution in the core. The liposome acts as the carrier of the active therapeutic agent.

The present description is further illustrated by the following examples, which should not be construed as limiting in any way. The contents of all cited references (including literature references, issued patents, published patent applications as cited throughout this application) are hereby expressly incorporated by reference.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Exemplification

Materials and Procedures

Peptides and proteins. Unlabeled UL54 peptide 1, corresponding to the 22 C-terminal residues of HCMV UL54 (Loregian et al., 2003), and the same peptide N-terminally labeled with the pentafluorofluorescein-derivative Oregon Green 514 (Molecular Probes) were synthesized and HPLC-purified by C. Dahl at the Biopolymers Facility of the Department of Biological Chemistry & Molecular Pharmacology (Harvard Medical School). Peptide A, corresponding to the 36 C-terminal residues of HSV-1 UL30 (Digard et al., 1995), and a peptide comprising the 18 C-terminal residues of HSV-1 UL30 (peptide E) and N-terminally labeled with Oregon Green 514 were prepared as described in Pilger et al. (Pilger et al., 2004). The peptides were dissolved in water, and concentration were determined by quantitative amino acid analysis performed by the Molecular Biology Core Facility, Dana-Farber Cancer Institute.

The wild-type GST-UL44ΔC290 fusion protein, which contains the N-terminal 290 residues of HCMV UL44, the GST-UL44ΔC290 I135A mutant, and GST alone, were purified from *E. coli* BL21 (DE3)pLysS harboring the appropriate plasmid, as described (Loregian et al., 2004a). The purification of MBP-UL42ΔC340 fusion protein, which contains the N-terminal 340 residues of HSV-1 UL42, has been previously described (Bridges et al., 2001). Purified baculovirus-expressed HCMV UL54 and UL44 proteins, prepared as described (Loregian et al., 2003), were kindly provided by H. S. Marsden (Institute of Virology, Glasgow, UK). Concentrations of all proteins were determined using quantitative amino acid analysis at the Molecular Biology Core Facility, Dana-Farber Cancer Institute.

FP assays. Unless otherwise indicated, 3 mM of Oregon Green-labeled peptide 1 was added to 2.5 μM GST-UL44ΔC290 in 50 mM Tris-HCl (pH 7.5), 2 mM dithiothreitol, 0.5 mM EDTA, 150 mM NaCl, 4% glycerol and 100 μg/ml bovine serum albumin and kept on ice until the mix was distributed into black 384-well plates (Nunc) in a total volume of 40 μl per well. For high throughput screening, small molecules (5 mg/ml in DMSO) of the Maybridge, Bionet, Peakdale, ChemDiv, and Chembridge Microformat libraries were obtained from the ICCB, and 100 nl of each compound were transferred to individual wells using 384-pin arrays. All compounds were tested in duplicate. As controls, reaction mixtures containing either labeled peptide 1 only, or GST-UL44ΔC290 plus labeled peptide 1 (no compound), or GST-UL44ΔC290 plus labeled peptide 1 in the presence of 3 μM or 20 μM of unlabeled peptide 1, were included on each screening plate. After 15-min incubation at room temperature, FP values were determined by using an Analyst plate reader (LJL Biosystems) at the ICCB.

Selected compounds were also tested in an FP assay used to detect inhibitors of HSV-1 DNA polymerase subunit interactions. The assay was conducted as described in Pilger et al. (Pilger et al., 2004), testing various concentrations of each compound in duplicate.

DNA polymerase assays. The effects of compounds were tested in an assay that measures long-chain DNA synthesis as described in Loregian et al. (Loregian et al., 2004a), with 5 µl of in vitro-transcribed and -translated UL54 plus 800 fmol of GST-UL44ΔC290 in the absence or in the presence of various amounts of each compound.

The basal DNA polymerase activity of UL54 in the absence or in the presence of various amounts of each compound was measured by a filter-based assay as previously described (Loregian et al., 2003), but using 5 µl of in vitro-transcribed and -translated UL54 as in Loregian et al. (Loregian et al., 2004a). The reaction was initiated by addition of a reaction mixture containing 75 mM Tris-HCl (pH 8.0), 6.5 mM $MgCl_2$, bovine serum albumin (400 µg/ml), 1.67 mM β-mercaptoethanol, 150 mM KCl, 1.6 µM [$^3$H]dTTP, poly(dA)-oligo(dT) (10 µg/ml; Amersham Pharmacia Biotech), and 0, 4, 20, 40, 100 µM of each compound. Samples were taken after 20 min of incubation at 37° C. and spotted onto DE81 filters (Whatman), previously soaked in 0.1 M EDTA and air dried. The filters were washed three times in 5% $Na_2HPO_4$, two times in water, and two times in methanol and then were dried. Radioactivity was measured with a scintillation counter.

UL54-UL44 interaction ELISA. This assay was conducted as described in (Loregian et al., 2003), testing various concentrations of each compound. After final washes, the chromogenic substrate 2,2'-azino-bis(3-ethylbenzothiazoline-6-sulphonic acid (ABTS, Pierce) in citrate phosphate buffer (pH 4.0) containing 0.01% hydrogen peroxide was added and absorbance was read at 405 nm on a Victor plate reader (Wallac).

Antiviral assays. Plaque reduction assays were performed essentially as follows: HFF (human foreskin fibroblast) cells were seeded at $2 \times 10^5$ cells per well in 24-well cluster dishes. The next day, cells were infected with HCMV (strain AD169) at 80 PFU per well in DMEM plus 5% fetal bovine serum (FBS) at 37° C. Two hours post-infection, the inocula were removed, cells were washed, and media containing various drug dilutions, 5% FBS, and 0.6% methylcellulose were added. All drug dilutions were tested at least in duplicate. After incubation at 37° C. for 10-11 days, cell monolayers were stained with crystal violet and plaques were counted under light microscopy. The number of plaques observed in the presence of each drug concentration was compared to the number observed in the absence of drug.

For yield reduction assays, HFF cells were plated at $2 \times 10^4$ cells per well in 96-well cluster dishes, incubated overnight, and infected with HCMV AD169 at a multiplicity of infection (MOI) of 1. After virus adsorption for 2 hr at 37° C., cells were washed and incubated with 200 µl of fresh media containing test compounds at increasing drug concentration. Plates were incubated for 3 or 5 days at 37° C. and subjected to one cycle of freezing and thawing, and titers were determined by transferring 100-µl aliquots from each of the wells to a fresh 96-well monolayer culture of HFF cells followed by 1:5 serial dilution across the plate. Cultures were incubated for 7 days, cells were stained, and the numbers of plaques were determined as described above.

Cytotoxicity assays. HFF cells were seeded at $2 \times 10^4$, $4 \times 10^3$, or $10^3$ cells per well into 96-well plates and, after a 3-hr incubation to allow cell attachment, were treated for 24, 72, or 120 hr, respectively, with various concentrations of each compound in duplicate. Cell viability was then determined with an XTT assay (Roche Molecular Biochemicals) according to the manufacturer's protocol by using a Victor plate reader (Wallac).

EXAMPLE 1

Identification of Compounds that Inhibit HCMV Polymerase Subunit Interactions

A fluorescence polarization (FP) assay was used to identify compounds that inhibit HCMV polymerase subunit interactions. Compounds from the Harvard Institute of Chemistry and Cell Biology (ICCB, Harvard Medical School) were screened as follows. 3 nM of a synthetic peptide corresponding to the C-terminal 22 residues of HMCV UL54 (termed peptide 1 in Loregian et al., J. Virol. 2003, 77:8336-8344) and N-terminally labeled with Oregon Green was added to 2.5 µM GST-UL44ΔC290 in 50 mM Tris-HCl (pH 7.5), 2 mM DTT, 0.5 mM EDTA, 150 mM NaCl, 4% Glycerol and 100 µg/ml bovine serum albumin and kept on ice until the mix was distributed into black 384-well plates (Nunc) in a total volume of 40 µl per well. Small molecules (5 mg/ml in DMSO) were obtained from the ICCB, and 100 nl of each compound was transferred to individual wells using 384-pin arrays. To ensure comparable data, internal reference values (peptide only, no compound, no DMSO) were included on each screening plate. After 5-min incubation at room temperature, the FP values were determined by using an Analyst plate reader (LJL Biosystems) at the ICCB.

The values are a measure of the interaction between the accessory protein UL44 of HCMV and the fluorescently labeled peptide from the catalytic subunit UL54 of the polymerase by the increase in FP. Compounds that score positive in this assay knock out the increase in FP.

The results, which are set forth in column 1 of Table 1 (FIG. 2), represent the concentrations of compounds that result in a 50% decrease IC50 in FP.

The effect of the compounds was also tested in an assay that measures long chain (Lc) DNA synthesis as described in Loregian et al., J. Virol. 2004, 78:158-167, but with 5 µl of in vitro-transcribed and -translated UL54 plus 800 fmol of GST-UL44ΔC290, in the absence or in the presence of different amounts (6.25, 12.5, 25, 50, 100 µM) of each compound.

In this assay, the combination of Pol and UL44 make long chains of DNA. The results, which are shown in column 4 of Table 1, indicate that compounds AL5, 9, 12, 18 and 21 have relatively low IC50s in this assay.

To determine if any of the compounds inhibit Pol rather than the interaction between UL44 and Pol, the activity of the compounds against the catalytic subunit of Pol, i.e., UL54, was determined as follows. The basal DNA polymerase activity of UL54 in the absence or in the presence of different amounts of each compound was measured by a filter-based assay as previously described (Loregian et al., J. Virol. 2003, 77:8336-8344), but with 3.5 µl of in vitro-transcribed and -translated UL54 as in Loregian et al., J. Virol. 2004, 78:158-167. The reaction was initiated by addition of a reaction mixture containing 75 mM Tris-HCl (pH 8.0), 6.5 mM $MgCl_2$, bovine serum albumin (400 µg/ml), 1.67 mM β-mercaptoethanol, 150 mM KCl, 1.6 µM [$^3$H]dTTP, poly(dA)-oligo(dT) (10 µg/ml; Amersham Pharmacia Biotech), and 0, 4, 20, 40, 100 µM of each compound. Samples were taken after 20 min of incubation at 37° C. and spotted onto DE81 filters (Whatman), previously soaked in 0.1 M EDTA and air dried. The filters were washed three times in 5% $Na_2HPO_4$, two times in water, and two times in methanol and then were dried. Radioactivity was measured with a scintillation counter.

The results, which are presented in the second column of Table 1, indicate that none of the compounds are potent in this assay, and that, therefore, all the compounds interfere with the interaction between UL44 and UL54.

Another assay that was used to test the effect of the compounds on the interaction of UL44 and UL54 is an ELISA interaction assay, which measures the interaction of the two full length proteins with each other. This assay was conducted as described in Loregian et al., J. Virol. 2003, 77:8336-8344, testing different concentrations (0, 3.12, 6.25, 12.5, 25, 50, 100, 200 µM) of each compound. The results, which are shown in column 5 of Table 1, indicate that compounds AL5, 9, 12, 18 and 21 are potent in this assay.

EXAMPLE 2

Measurement of IC50s in a Plaque Reduction Assay

The effect of the compounds was assessed in a plaque reduction assay that measures the number of plaques formed in the presence of varying concentrations of a drug, as follows. HFF were seeded at $2 \times 10^5$ cells per well in 24-well cluster dishes. The next day, they were infected with HCMV AD169 at 80 PFU per well in DMEM plus 5% FBS at 37° C. Two hr post-infection, the inocula were then removed, cells were washed, and media containing selected drug dilutions (0, 0.1, 0.3, 1, 3, 10, 30 µM), and 5% FBS and 0.6% methylcellulose were added. All drug dilutions were tested at least in duplicate. After incubation at 37° C. for 10-11 days, cell monolayers were stained with crystal violet and plaques were enumerated under light microscopy. The number of plaques observed in the presence of each drug concentration was compared to the number observed in the absence of drug.

The results, which are shown in column 9 of Table 1, indicate that compounds AL5, 9, 12, 18, 20 and 21 have relatively low IC50s, some of which are about 1 micromolar.

EXAMPLE 3

Measurement of the Cytotoxicity of the Compounds

The cytotoxicity of the compounds was measured in an XTT assay. XTT is a compound that is converted to a product that can be measured calorimetrically, but only by viable cells. This assay is as follows. HFF (human foreskin fibroblasts) cells were seeded at different concentrations into 96-well plates and treated with various concentrations (from 0 to 200 µM) of each compound in duplicate for 24, 72 or 120 hr. Cell viability was then determined with an XTT assay (Roche Molecular Biochemicals) according to the manufacturer's protocol by using a Victor plate reader (Wallac).

The results, which are shown in columns 6, 7, and 8, indicate the concentrations (CC50) that result in the loss of 50% of the viable cells after the indicated times of treatment. The results indicate that compounds AL5, 9, 12, 18, 20 and 21 have relatively high CC50's.

EXAMPLE 4

Measurement of IC50s in an Assay of Virus Yield

The effect of the compounds was assessed in an assay of virus yield. In this assay, cells are infected at a relatively high multiplicity of infection (about one per cell) and then drug is added. The virus produced at the different times post infection is measured. 120 hrs. is about the peak titer. This assay was conducted as follows. HFF cells were plated at 20,000 cells per well in 96-well cluster dishes, incubated overnight, and infected with HCMV AD169 at an MOI of 1. After virus adsorption for 2 hr at 37° C., cells were washed and incubated with 200 µl of fresh media containing test compounds at 0.1, 0.3, 1, 3, 10, 30 µM drug concentration. Plates were incubated for 3 or 5 days at 37° C. and subjected to one cycle of freezing and thawing, and titers were determined by transferring 100-µl aliquots from each of the wells to a fresh 96-well monolayer culture of HFF cells followed by 1:5 serial dilution across the plate. Cultures were incubated for 7 days, cells were stained, and the numbers of plaques were determined as described above.

The results, which are shown in column 10 of Table 1, indicate that compounds AL5, 9, 12, 18, 20 and 21 exhibit relatively low IC50s, with AL18 being submicromolar and its cytotoxicity for 120 hrs being 200 micromolar. These results appear to compare favorably with ganciclovir.

EXAMPLE 5

Specificity of the Compounds Toward HCMV

The compounds were tested in an FP assay for the HSV polymerase subunits. The assay was conducted as described in Pilger et al., Chem. Biol. 2004, 11:647-654, testing various concentrations (0, 4, 50, 200 µM) of each compound in duplicate. The results indicate that the compounds do not inhibit the interaction between the polymerase subunits of HSV.

EXAMPLE 6

New Selective Anti-cytomegalovirus Compounds Discovered by Screening for Inhibitors of Subunit Interactions of the Viral Polymerase This Example reiterates in part some of the results described above.

There is a need to develop new drugs against human cytomegalovirus (HCMV), a pathogen responsible for severe diseases in immunocompromised hosts and in newborn children. We investigated whether new inhibitors of HCMV replication could be discovered by screening for compounds that disrupt the interaction between the accessory subunit of the viral DNA polymerase and the catalytic subunit. From ~50,000 small molecules, we identified five structurally diverse compounds that specifically interfere with this interaction and its functional consequences. These five compounds also inhibited HCMV replication with sub-to low micromolar potency, and at concentrations up to 500-fold lower than those at which they exhibited cytotoxicity. These new compounds represent a promising starting point for the development of new antiviral drugs.

REFERENCES

Archakov A I, Govorun V M, Dubanov A V, Ivanov Y D, Veselovsky A V, Lewi P, Janssen P. 2003. Protein-protein interactions as a target for drugs in proteomics. Proteomics 3(4):380-391.

Arkin M R, Wells J A. 2004. Small-molecule inhibitors of protein-protein interactions: progressing towards the dream. Nat Rev Drug Discov 3(4):301-317.

Bridges K G, Chow C S, Coen D M. 2001. Identification of crucial hydrogen-bonding residues for the interaction of herpes simplex virus DNA polymerase subunits via peptide display, mutational, and calorimetric approaches. J Virol 75(11):4990-4998.

Bridges K G, Hua Q, Brigham-Burke M R, Martin J D, Hensley P, Dahl C E, Digard P, Weiss M A, Coen D M. 2000. Secondary structure and structure-activity relationships of peptides corresponding to the subunit interface of herpes simplex virus DNA polymerase. J Biol Chem 275 (1):472-478.

Cihlar T, Fuller M D, Chemington J M. 1997. Expression of the catalytic subunit (UL54) and the accessory protein (UL44) of human cytomegalovirus DNA polymerase in a coupled in vitro transcription/translation system. Protein Expr Purif 11(2):209-218.

Cochran A G. 2000. Antagonists of protein-protein interactions. Chem Biol 7(4):R85-94.

Coen D M, Schaffer P A. 2003. Antiherpesvirus drugs: a promising spectrum of new drugs and drug targets. Nat Rev Drug Discov 2(4):278-288.

Cunningham B C, Wells J A. 1997. Minimized proteins. Curr Opin Struct Biol 7(4):457-462.

Dandliker W B, Hsu M L, Levin J, Rao R. 1981. Equilibrium and kinetic inhibition assays based upon fluorescence polarization. Methods Enzymol 74 Pt C:3-28.

Digard P, Williams K P, Hensley P, Brooks I S, Dahl C E, Coen D M. 1995. Specific inhibition of herpes simplex virus DNA polymerase by helical peptides corresponding to the subunit interface. Proc Natl Acad Sci USA 92(5):1456-1460.

Ertl P F, Powell K L. 1992. Physical and functional interaction of human cytomegalovirus DNA polymerase and its accessory protein (ICP36) expressed in insect cells. J Virol 66(7):4126-4133.

Eubanks S, Nguyen T L, Peyton D, Breslow E. 2000. Modulation of dimerization, binding, stability, and folding by mutation of the neurophysin subunit interface. Biochemistry (Mosc) 39(27):8085-8094.

Faulds D, Heel R C. 1990. Ganciclovir. A review of its antiviral activity, pharmacokinetic properties and therapeutic efficacy in cytomegalovirus infections. Drugs 39(4):597-638.

Imai Y, Moralez A, Andag U, Clarke J B, Busby W H, Jr., Clemmons D R. 2000. Substitutions for hydrophobic amino acids in the N-terminal domains of IGFBP-3 and -5 markedly reduce IGF-I binding and alter their biologic actions. J Biol Chem 275(24):18188-18194.

Koltzscher M, Gerke V. 2000. Identification of hydrophobic amino acid residues involved in the formation of S100P homodimers in vivo. Biochemistry (Mosc) 39(31):9533-9539.

Kouzarides T, Bankier A T, Satchwell S C, Weston K, Tomlinson P, Barrell B G. 1987. Sequence and transcription analysis of the human cytomegalovirus DNA polymerase gene. J Virol 61(1):125-133.

Lomax M E, Barnes D M, Hupp T R, Picksley S M, Camplejohn R S. 1998. Characterization of p53 oligomerization domain mutations isolated from Li-Fraumeni and Li-Fraumeni like family members. Oncogene 17(5):643-649.

Loregian A, Appleton B A, Hogle J M, Coen D M. 2004a. Residues of human cytomegalovirus DNA polymerase catalytic subunit UL54 that are necessary and sufficient for interaction with the accessory protein UL44. J Virol 78(1): 158-167.

Loregian A, Appleton B A, Hogle J M, Coen D M. 2004b. Specific residues in the connector loop of the human cytomegalovirus DNA polymerase accessory protein UL44 are crucial for interaction with the UL54 catalytic subunit. J Virol 78(17):9084-9092.

Loregian A, Marsden H S, Palu G. 2002. Protein-protein interactions as targets for antiviral chemotherapy. Rev Med Virol 12(4):239-262.

Loregian A, Rigatti R, Murphy M, Schievano E, Palu G, Marsden H S. 2003. Inhibition of human cytomegalovirus DNA polymerase by C-terminal peptides from the UL54 subunit. J Virol 77(15):8336-8344.

Markham A, Faulds D. 1994. Ganciclovir. An update of its therapeutic use in cytomegalovirus infection. Drugs 48(3): 455-484.

Nishiyama Y, Maeno K, Yoshida S. 1983. Characterization of human cytomegalovirus-induced DNA polymerase and the associated 3'-to-5', exonuclease. Virology 124(2):221-231.

Pari G S, Anders D G. 1993. Eleven loci encoding transacting factors are required for transient complementation of human cytomegalovirus oriLyt-dependent DNA replication. J Virol 67(12):6979-6988.

Pari G S, Kacica M A, Anders D G. 1993. Open reading frames UL44, IRS1/TRS1, and UL36-38 are required for transient complementation of human cytomegalovirus ori-Lyt-dependent DNA synthesis. J Virol 67(5):2575-2582.

Pilger B D, Cui C, Coen D M. 2004. Identification of a small molecule that inhibits herpes simplex virus DNA Polymerase subunit interactions and viral replication. Chem Biol 11(5):647-654.

Ramadevi N, Rodriguez J, Roy P. 1998. A leucine zipper-like domain is essential for dimerization and encapsidation of bluetongue virus nucleocapsid protein VP4. J Virol 72(4): 2983-2990.

Reusser P. 1996. Herpesvirus resistance to antiviral drugs: a review of the mechanisms, clinical importance and therapeutic options. J Hosp Infect 33(4):235-248.

Ripalti A, Boccuni M C, Campanini F, Landini M P. 1995. Cytomegalovirus-mediated induction of antisense mRNA expression to UL44 inhibits virus replication in an astrocytoma cell line: identification of an essential gene. J Virol 69(4):2047-2057.

Sengchanthalangsy L L, Datta S, Huang D B, Anderson E, Braswell E H, Ghosh G. 1999. Characterization of the dimer interface of transcription factor NFkappaB p50 homodimer. J Mol Biol 289(4):1029-1040.

Snoeck R, Sakuma T, De Clercq E, Rosenberg I, Holy A. 1988. (S)-1-(3-hydroxy-2-phosphonylmethoxypropyl)cytosine, a potent and selective inhibitor of human cytomegalovirus replication. Antimicrob Agents Chemother 32(12):1839-1844.

Stenberg G, Abdalla A M, Mannervik B. 2000. Tyrosine 50 at the subunit interface of dimeric human glutathione transferase P1-1 is a structural key residue for modulating protein stability and catalytic function. Biochem Biophys Res Commun 271(1):59-63.

Thomas M C, Ballantine S P, Bethell S S, Bains S, Kellam P, Delves C J. 1998. Single amino acid substitutions disrupt tetramer formation in the dihydroneopterin aldolase enzyme of *Pneumocystis carinii*. Biochemistry (Mosc) 37(33):11629-11636.

Toogood P L. 2002. Inhibition of protein-protein association by small molecules: approaches and progress. J Med Chem 45(8):1543-1558. Trincado D E, Scott G M, White P A, Hunt C, Rasmussen L, Rawlinson W D. 2000. Human cytomegalovirus strains associated with congenital and perinatal infections. J Med Virol 61(4):481-487.

Tsai C J, Lin S L, Wolfson H J, Nussinov R. 1997. Studies of protein-protein interfaces: a statistical analysis of the hydrophobic effect. Protein Sci 6(1):53-64.

Weiland K L, Oien N L, Homa F, Wathen M W. 1994. Functional analysis of human cytomegalovirus polymerase accessory protein. Virus Res 34(3):191-206.

Zuccola H J, Filman D J, Coen D M, Hogle J M. 2000. The crystal structure of an unusual processivity factor, herpes simplex virus UL42, bound to the C terminus of its cognate polymerase. Mol Cell 5(2):267-278.

Pass, R. F. (2001). Cytomegalovirus. In Fields Virology, 4th ed., D. M. Knipe, P. M. Howley, D. E. Griffin, R. A. Lamb, M. A. Martin, B. Roizman, & S. E. Straus. eds. (Philadelphia: Lippincott Williams & Wilkins) vol 2, pp 1586-1705.

Coen, D. M. (1992). Molecular aspects of antiherpesvirus drugs. Semin. Virol. 3, 3-12.

Stinski M. F. (1983). Molecular biology of cytomegaloviruses. In Herpesviruses, B.

Roizman. ed. (New York: Plenum Press) vol 2, pp 67-113.

EQUIVALENTS

Those skilled in the art will recognize, or be able to ascertain using no more than routine experimentation, many equivalents of the specific embodiments described herein. Such equivalents are intended to be encompassed by the following claims.

We claim:

1. A method of treating an infection by human cytomegalovirus (HCMV) in a subject comprising administering to the subject in need thereof an effective amount of

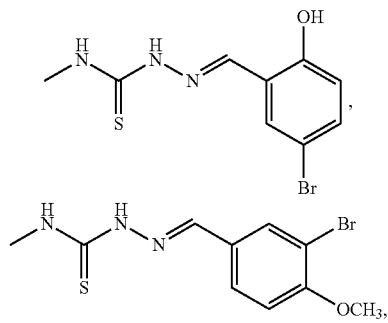

or a pharmaceutically acceptable salt thereof.

2. The method of claim 1, wherein the subject is an immunosuppressed subject.

3. The method of claim 2, wherein the subject is infected with human immunodeficiency virus (HIV).

* * * * *